(12) United States Patent
Geho et al.

(10) Patent No.: US 9,943,602 B2
(45) Date of Patent: Apr. 17, 2018

(54) ORALLY BIOAVAILABLE LIPID-BASED CONSTRUCTS

(71) Applicant: SDG, INC., Cleveland, OH (US)

(72) Inventors: W. Blair Geho, Wooster, OH (US); John R. Lau, Howard, OH (US)

(73) Assignee: SDG, Inc., Cleveland, OH (US)

( * ) Notice: Subject to any disclaimer, the term of this patent is extended or adjusted under 35 U.S.C. 154(b) by 360 days.

(21) Appl. No.: 14/268,728

(22) Filed: May 2, 2014

(65) Prior Publication Data

US 2014/0243430 A1 Aug. 28, 2014

Related U.S. Application Data

(63) Continuation of application No. 12/816,009, filed on Jun. 15, 2010, now Pat. No. 8,846,053, which is a continuation-in-part of application No. 12/732,952, filed on Mar. 26, 2010, now Pat. No. 9,145,453, which is a continuation-in-part of application No. PCT/US2008/077990, filed on Sep. 26, 2008, which is a continuation-in-part of application No. 11/904,937, filed on Sep. 28, 2007, now Pat. No. 8,962,015.

(51) Int. Cl.
| | | |
|---|---|---|
| A61K 36/28 | (2006.01) | |
| A61K 47/28 | (2006.01) | |
| A61K 31/198 | (2006.01) | |
| A61K 31/4045 | (2006.01) | |
| A61K 31/4188 | (2006.01) | |
| C07K 16/00 | (2006.01) | |
| A61K 47/24 | (2006.01) | |
| A23L 33/10 | (2016.01) | |
| A61K 47/54 | (2017.01) | |
| A61K 9/127 | (2006.01) | |
| A61K 9/48 | (2006.01) | |
| A61K 39/00 | (2006.01) | |

(52) U.S. Cl.
CPC ............ *A61K 47/28* (2013.01); *A23L 33/10* (2016.08); *A61K 31/198* (2013.01); *A61K 31/4045* (2013.01); *A61K 31/4188* (2013.01); *A61K 47/24* (2013.01); *A61K 47/544* (2017.08); *A61K 47/557* (2017.08); *C07K 16/00* (2013.01); *A23V 2002/00* (2013.01); *A61K 9/127* (2013.01); *A61K 9/4858* (2013.01); *A61K 2039/505* (2013.01); *A61K 2039/542* (2013.01)

(58) Field of Classification Search
None
See application file for complete search history.

(56) References Cited

U.S. PATENT DOCUMENTS

| | | |
|---|---|---|
| 4,501,728 A | 2/1985 | Geho et al. |
| 4,603,044 A | 7/1986 | Geho et al. |
| 4,740,375 A | 4/1988 | Geho et al. |
| 4,946,787 A | 8/1990 | Eppstein et al. |
| 5,104,661 A | 4/1992 | Lau |
| 5,411,730 A | 5/1995 | Kirpotin et al. |
| 5,567,432 A | 10/1996 | Lau et al. |
| 5,795,895 A | 8/1998 | Anchors |
| 6,063,400 A | 5/2000 | Geho et al. |
| 6,177,099 B1 | 1/2001 | Lau et al. |
| 6,365,156 B1 | 4/2002 | Lee |
| 6,726,924 B2 | 4/2004 | Keller |
| 7,169,410 B1 | 1/2007 | Lau et al. |
| 8,846,053 B2 | 9/2014 | Geho et al. |
| 2003/0133972 A1 | 7/2003 | Danthi et al. |
| 2004/0016035 A1 | 1/2004 | Floyd |
| 2005/0026826 A1 | 2/2005 | Hoenig |
| 2005/0059100 A1 | 3/2005 | Meares et al. |
| 2006/0008461 A1 | 1/2006 | Yatvin et al. |
| 2006/0009381 A1 | 1/2006 | Reutelingsperger |
| 2006/0141047 A1* | 6/2006 | Heller ............... A61K 9/0019 424/489 |
| 2006/0222697 A1 | 10/2006 | Lau et al. |
| 2006/0222698 A1 | 10/2006 | Lau et al. |
| 2006/0127361 A1 | 11/2006 | Lau et al. |
| 2007/0104777 A1 | 5/2007 | Lau et al. |
| 2007/0218117 A1 | 9/2007 | Lau et al. |
| 2007/0281325 A1 | 12/2007 | Danielzadeh |
| 2008/0014255 A1 | 1/2008 | Tagawa et al. |
| 2008/0050372 A1* | 2/2008 | Grunberger ......... C07K 14/473 424/133.1 |
| 2008/0305156 A1 | 12/2008 | Laing et al. |
| 2009/0087479 A1 | 4/2009 | Lau et al. |

FOREIGN PATENT DOCUMENTS

| | | |
|---|---|---|
| JP | 11-116478 | 4/1999 |
| JP | 11116478 A * | 4/1999 |
| WO | 1999/059545 A1 | 11/1999 |
| WO | 2006/127361 A2 | 11/2006 |

(Continued)

OTHER PUBLICATIONS

Database GNPD (online) Mintel, "Children's Century Junior Complete Chewable Tablets," XP002743190, Database Accession No. 1249200, 2010.
Database GNPD (online), MINTEL, "Colostrom Plus 1 Baby Formula," XP002743191, Database Accession No. 1495943, 2009.
Database GNPD (online) MINTEL, "Chocolate Fudge Meal Bars," XP002743192, Database Accession No. 877328, 2007.
Database GNPD (online) MINTEL, "Dietary Supplement," XP002743193, Database Accession No. 1128643, 2009.
Cantenys, D. et al., "Covalent Attachment of Insulin to the Outer Surface of Liposomes," Biochemical and Biophysical Research Communications, 1983, vol. 117, No. 2, pp. 399-405.

(Continued)

*Primary Examiner* — Chris R Tate
*Assistant Examiner* — Randall Winston
(74) *Attorney, Agent, or Firm* — Saul Ewing Arnstein & Lehr LLP; Kathryn Doyle; Domingos J. Silva

(57) ABSTRACT

The present invention is embodied by a composition capable inducing weight loss in a patient in need thereof.

9 Claims, 20 Drawing Sheets

(56) References Cited

FOREIGN PATENT DOCUMENTS

WO    2009/042945 A1    4/2009
WO    2010/111271 A1    9/2010

OTHER PUBLICATIONS

Erion, M.D. et al., "Targeting Thyroid Hormone Receptor-B Agonists to the Liver Reduces Cholesterol and Triglycerides and Improves the Therapeutic Index," PNAS, 2007, vol. 104, No. 39, pp. 15490-15495.
Hermanson, G.T., "Bioconjugate Techniques," 2nd Edition, 2008, pp. 278-291, 294-295, 300-301, 304-321, 881 and 895-899.
Takeoka, S. et al., "Rolling Properties of rGPlb alpha-Conjugated Phospholipid Vesicles with Different Membrane Flexibilities on vWf Surface Under Flow Conditions," Biochemical and Biophysical Research Communications, 2002, vol. 296, pp. 765-770.
Dong, C. et al., "Acacia-Gelatin Microencapsulated Liposomes: Preparation, Stability, and Release of Acetylsalicylic Acid," Pharmaceutical Research, 1993, vol. 10, No. 1, pp. 141-146.

* cited by examiner

Oral Absorption of Composition - Intact Fasted Rats

ORAL ABSORPTION OF COMPOSITION FROM NORMAL RATS DRINKING WATER

Body Weight Loss In Type 2 Diabetics 18 Weeks

7 Point Blood Glucose in 18 Week Data – Intent to Treat

ORALLY BIOAVAILABLE LIPID-BASED CONSTRUCTS

CROSS-REFERENCE TO RELATED APPLICATIONS

The present application is a continuation of, and claims priority to, U.S. application Ser. No. 12/816,009, now allowed, which is a continuation-in-part of, and claims priority to, U.S. patent application Ser. No. 12/732,952, filed Mar. 26, 2010, which is a continuation-in-part of, and claims priority to, PCT Application No. PCT/US08/77990, filed Sep. 26, 2008, which is a continuation-in-part of, and claims priority to, U.S. patent application Ser. No. 11/904,937, filed Sep. 28, 2007, all of which applications are incorporated herein by reference in their entireties.

BACKGROUND OF THE INVENTION

One of the most preferred ways to deliver a pharmaceutical to a subject is in an oral formulation. However, oral formulations of many pharmaceutical compounds are often unavailable due to the pharmaceutical's incompatibility with the harsh environment of the digestive tract. This is particularly true for pharmaceutical compounds such as peptides, proteins, certain small molecules, and nucleic acids.

Another issue plaguing oral delivery is the quantity of medication that must be both orally administered to affect the desired outcome in a patient. For example, poor bioavailability due to a bad solubility profile can mean that even though a certain medication tolerates the digestive milieu, it cannot be given orally in any meaningful way. It may, for example, need to be given in a substantially larger doses than would be required if given intravenously, or via another route of administration.

D-biotin is an example of a compound that, while susceptible to oral delivery, has a poor solubility profile. As a result, the amount of material that must be given to ensure activity in general, and in particular at the liver, is substantially larger than preferred. Thus, what is needed in the field of biotin delivery, is a composition capable of affecting efficient oral delivery of biotin and a biotin-derived compounds. The present invention meets these needs.

BRIEF SUMMARY OF THE INVENTION

The present invention includes compositions that facilitate and/or enable efficient oral absorption of biotin or biotin-derived compounds that are not presently efficiently processed by the body when given alone. The various compositions of the invention described herein have been found to improve biotin bioavailability by substantially increasing solubility. In addition, the compositions described herein have been surprisingly found to affect weight loss in patients in need thereof at a dose that is substantially reduced from what was previously known in the prior art.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

DETAILED DESCRIPTION OF THE INVENTION

Figure 1:
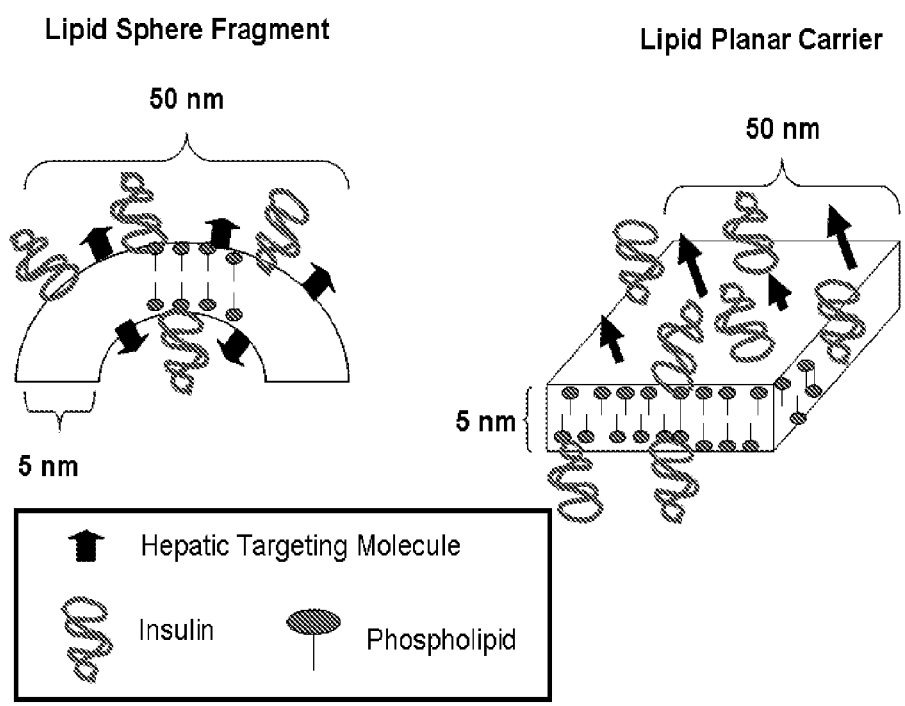
FIG. 1 is a schematic representation of a composition of the invention.

The present invention includes compositions that facilitate and/or enable efficient oral absorption of biotin or biotin-derived compounds that are not presently efficiently processed by the body when given alone. The various compositions of the invention described herein have been found to improve biotin bioavailability by substantially increasing solubility. In addition, the compositions described herein have been surprisingly found to affect weight loss in patients in need thereof at a dose that is substantially reduced from what was previously known in the prior art.

In one embodiment, a composition of the invention comprises various lipid components (which can themselves be members of a liposome or liposome fragment), an optional targeting agent, D-biotin, and gelatin. In this embodiment, the composition associates with D-biotin, and chaperones it through the lumen of the gut into the portal blood flow and finally on to the systemic circulation. In other embodiments, the composition of the invention comprises various lipid components, a biotin-derived targeting agent, and gelatin.

In some embodiments, a composition of the invention can comprise gelatin and about 56 mole percent 1,2 distearoyl-sn-glycero-3-phosphocholine, about 21 mole percent dihexadecyl phosphate, about 15 mole percent cholesterol, and about 8 mole percent of a biotin-derived targeting agent.

In some embodiments, the biotin-derived targeting agent is selected from the group consisting of N-hydroxysuccinimide (NHS) biotin; sulfo-NHS-biotin; N-hydroxysuccinimide long chain biotin; sulfo-N-hydroxysuccinimide long chain biotin; D-biotin; biocytin; sulfo-N-hydroxysuccinimide-S—S-biotin; biotin-BMCC; biotin-HPDP; iodoacetyl-LC-biotin; biotin-hydrazide; biotin-LC-hydrazide; biocytin hydrazide; biotin cadaverine; carboxybiotin; photobiotin; ρ-aminobenzoyl biocytin trifluoroacetate; ρ-diazobenzoyl biocytin; biotin DHPE; biotin-X-DHPE; 12-((biotinyl)amino)dodecanoic acid; 12-((biotinyl)amino)dodecanoic acid succinimidyl ester; S-biotinyl homocysteine; biocytin-X; biocytin x-hydrazide; biotinethylenediamine; biotin-XL; biotin-X-ethylenediamine; biotin-XX hydrazide; biotin-XX-SE; biotin-XX, SSE; biotin-X-cadaverine; α-(t-BOC)biocytin; N-(biotinyl)-N'-(iodoacetyl) ethylenediamine; DNP-X-biocytin-X-SE; biotin-X-hydrazide; norbiotinamine hydrochloride; 3-(N-maleimidylpropionyl)biocytin; ARP; biotin-1-sulfoxide; biotin methyl ester; biotin-maleimide; biotin-poly(ethyleneglycol)amine; (+) biotin 4-amidobenzoic acid sodium salt; Biotin 2-N-acetylamino-2-deoxy-β-D-glucopyranoside; Biotin-α-D-N-acetylneuraminide; Biotin-α-L-fucoside; Biotin lacto-N-bioside; Biotin-Lewis-A trisaccharide; Biotin-Lewis-Y tetrasaccharide; Biotin-α-D-mannopyranoside; biotin 6-O-phospho-α-D-mannopyranoside; and 1,2-dipalmitoyl-sn-glycero-3-phosphoethanolamine-N-(biotinyl), iminobiotin derivatives of the aforementioned compounds, and mixtures thereof.

In particular embodiments, the biotin-derived targeting agent is D-biotin, biotin DHPE, or biotin-X-DHPE.

The present invention also provides a method for making an orally bioavailable composition comprising gelatin and about 56 mole percent 1,2 distearoyl-sn-glycero-3-phosphocholine, about 21 mole percent dihexadecyl phosphate, about 15 mole percent cholesterol, and about 8 mole percent of a biotin-derived targeting agent. The method can comprise the steps of mixing said 1,2 distearoyl-sn-glycero-3-phosphocholine, dihexadecyl phosphate, cholesterol and said at least one biotin-derived targeting agent in aqueous media to form a mixture; adding said mixture to gelatin to form a gelatin-associated mixture; and drying said gelatin-associated mixture.

In particular embodiments of the method described herein, the biotin-derived targeting agent is selected from the group consisting of D-biotin, biotin DHPE, and biotin-X-DHPE.

The present invention also provides a method of affecting weight loss in a patient, said method comprising administering to said patient an effective amount of an orally bioavailable composition comprising gelatin and about 56 mole percent 1,2 distearoyl-sn-glycero-3-phosphocholine, about 21 mole percent dihexadecyl phosphate, about 15 mole percent cholesterol, and about 8 mole percent of a biotin-derived targeting agent.

In certain embodiments of the method of affecting weight loss, the biotin-derived targeting agent is D-biotin, biotin DHPE, or biotin-X-DHPE.

In another embodiment of the invention, the composition of the invention further comprises D-biotin.

In an embodiment, a method of the invention includes co-administering at least one therapeutic agent useful for inducing weight loss In some embodiments, the at least one therapeutic agent useful for inducing weight loss is orlistat, sibutramine, phendimetrazine tartrate, methamphetamine, IONAMIN™, phentermine, fenfluramine, dexfenfluramine, chitosan, chromium picolinate, conjugated linoleic acid, green tea extract, guar gum, hoodia, a combination of topiramate and phentermine, a combination of bupropion and zonisamide, a combination of bupropion and naltrexone, a combination of phentermine and fluoxetine, a combination of phentermine and sertraline, a combination of phentermine and citalopram, a combination of phentermine and escitalopram, or a combination of phentermine and trazodone.

In one embodiment, the invention is a food additive, dietary supplement, or beverage additive comprising gelatin and about 56 mole percent 1,2 distearoyl-sn-glycero-3-phosphocholine, about 21 mole percent dihexadecyl phosphate, about 15 mole percent cholesterol, and about 8 mole percent of a targeting agent.

In some embodiments, the biotin-derived targeting agent is selected from the group consisting of N-hydroxysuccinimide (NHS) biotin; sulfo-NHS-biotin; N-hydroxysuccinimide long chain biotin; sulfo-N-hydroxysuccinimide long chain biotin; D-biotin; biocytin; sulfo-N-hydroxysuccinimide-S—S-biotin; biotin-BMCC; biotin-HPDP; iodoacetyl-LC-biotin; biotin-hydrazide; biotin-LC-hydrazide; biocytin hydrazide; biotin cadaverine; carboxybiotin; photobiotin; ρ-aminobenzoyl biocytin trifluoroacetate; ρ-diazobenzoyl biocytin; biotin DHPE; biotin-X-DHPE; 12-((biotinyl)amino)dodecanoic acid; 12-((biotinyl)amino)dodecanoic acid succinimidyl ester; S-biotinyl homocysteine; biocytin-X; biocytin x-hydrazide; biotinethylenediamine; biotin-XL; biotin-X-ethylenediamine; biotin-XX hydrazide; biotin-XX-SE; biotin-XX, SSE; biotin-X-cadaverine; α-(t-BOC)biocytin; N-(biotinyl)-N'-(iodoacetyl) ethylenediamine; DNP-X-biocytin-X-SE; biotin-X-hydrazide; norbiotinamine hydrochloride; 3-(N-maleimidylpropionyl)biocytin; ARP; biotin-1-sulfoxide; biotin methyl ester; biotin-maleimide; biotin-poly(ethyleneglycol)amine; (+) biotin 4-amidobenzoic acid sodium salt; Biotin 2-N-acetylamino-2-deoxy-β-D-glucopyranoside; Biotin-α-D-N-acetylneuraminide; Biotin-α-L-fucoside; Biotin lacto-N-bioside; Biotin-Lewis-A trisaccharide; Biotin-Lewis-Y tetrasaccharide; Biotin-α-D-mannopyranoside; biotin 6-O-phospho-α-D-mannopyranoside; and 1,2-dipalmitoyl-sn-glycero-3-phosphoethanolamine-N-(biotinyl), iminobiotin derivatives of the aforementioned compounds, and mixtures thereof.

In other embodiments, the biotin-derived targeting agent is D-biotin, biotin DHPE, or biotin-X-DHPE.

The present invention further provides a method of maintaining the weight of a patient in need thereof, comprising administering a compound comprising gelatin and about 56 mole percent 1,2 distearoyl-sn-glycero-3-phosphocholine, about 21 mole percent dihexadecyl phosphate, about 15 mole percent cholesterol, and about 8 mole percent of a targeting agent.

In some embodiments, the biotin-derived targeting agent is selected from the group consisting of N-hydroxysuccinimide (NHS) biotin; sulfo-NHS-biotin; N-hydroxysuccinimide long chain biotin; sulfo-N-hydroxysuccinimide long chain biotin; D-biotin; biocytin; sulfo-N-hydroxysuccinimide-S—S-biotin; biotin-BMCC; biotin-HPDP; iodoacetyl-LC-biotin; biotin-hydrazide; biotin-LC-hydrazide; biocytin hydrazide; biotin cadaverine; carboxybiotin; photobiotin; ρ-aminobenzoyl biocytin trifluoroacetate; ρ-diazobenzoyl biocytin; biotin DHPE; biotin-X-DHPE; 12-((biotinyl)amino)dodecanoic acid; 12-((biotinyl)amino)dodecanoic acid succinimidyl ester; S-biotinyl homocysteine; biocytin-X; biocytin x-hydrazide; biotinethylenediamine; biotin-XL; biotin-X-ethylenediamine; biotin-XX hydrazide; biotin-XX-SE; biotin-XX, SSE; biotin-X-cadaverine; α-(t-BOC)biocytin; N-(biotinyl)-N'-(iodoacetyl) ethylenediamine; DNP-X-biocytin-X-SE; biotin-X-hydrazide; norbiotinamine hydrochloride; 3-(N-maleimidylpropionyl)biocytin; ARP; biotin-1-sulfoxide; biotin methyl ester; biotin-maleimide; biotin-poly(ethyleneglycol)amine; (+) biotin 4-amidobenzoic acid sodium salt; Biotin 2-N-acetylamino-2-deoxy-β-D-glucopyranoside; Biotin-α-D-N-acetylneuraminide; Biotin-α-L-fucoside; Biotin lacto-N-bioside; Biotin-Lewis-A trisaccharide; Biotin-Lewis-Y tetrasaccharide; Biotin-α-D-mannopyranoside; biotin 6-O-phospho-α-D-mannopyranoside; and 1,2-dipalmitoyl-sn-glycero-3-phosphoethanolamine-N-(biotinyl), iminobiotin derivatives of the aforementioned compounds, and mixtures thereof.

In particular embodiments, the biotin-derived targeting agent is D-biotin, biotin DHPE, or biotin-X-DHPE.

Definitions

Unless defined otherwise, all technical and scientific terms used herein generally have the same meaning as commonly understood by one of ordinary skill in the art to which the invention belongs. Generally, the nomenclature used herein and the laboratory procedures in organic chemistry and protein chemistry are those well known and commonly employed in the art.

The articles "a" and "an" are used herein to refer to one or to more than one (i.e. to at least one) of the grammatical object of the article. By way of example, "an element" means one element or more than one element.

As used herein, amino acids are represented by the full name thereof, by the three-letter code as well as the one-letter code corresponding thereto, as indicated in the following table:

| Full Name | 3 Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Cystine | Cys-Cys | C-C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The term "lower", when used in reference to a chemical structure, describes a group containing from 1 to 6 carbon atoms.

The term "alkyl", by itself or as part of another substituent means, unless otherwise stated, a straight, branched or cyclic hydrocarbon having the number of carbon atoms designated (i.e. $C_1$-$C_6$ means one to six carbons). Examples include: methyl, ethyl, propyl, isopropyl, butyl, isobutyl, tert-butyl, pentyl, neopentyl, hexyl, cyclohexyl and cyclopropylmethyl. Most preferred is ($C_1$-$C_3$) alkyl, particularly ethyl, methyl and isopropyl.

The term "alkylene", by itself or as part of another substituent means, unless otherwise stated, a straight, branched or cyclic chain hydrocarbon having two substitution sites, e.g., methylene (—$CH_2$—), ethylene (—$CH_2CH_2$—), isopropylene (—$C(CH_3)$=CH—), etc.

The term "aryl", employed alone or in combination with other terms, means, unless otherwise stated, a carbocyclic structure, with or without saturation, containing one or more rings (typically one, two or three rings) wherein said rings may be attached together in a pendant manner, such as a biphenyl, or may be fused, such as naphthalene. Examples include phenyl, anthracyl, and naphthyl. The structure may be optionally substituted with one or more substituents, independently selected from halogen; ($C_1$-$C_6$)alkyl; ($C_1$-$C_6$)alkenyl; ($C_1$-$C_6$)alkoxy; OH; $NO_2$; C≡N; C(=O)O($C_1$-$C_3$)alkyl; ($C_2$-$C_6$)alkylene-$OR^2$; phosphonato; $NR^2_2$; NHC(=O)($C_1$-$C_6$)alkyl; sulfamyl; carbamyl; OC(=O)($C_1$-$C_3$)alkyl; O($C_2$-$C_6$)alkylene-N(($C_1$-$C_6$)alkyl)$_2$; and ($C_1$-$C_3$) perfluoroalkyl.

The term "arylloweralkyl" means a functional group wherein an aryl group is attached to a lower alkylene group, e.g., —$CH_2CH_2$-phenyl.

The term "alkoxy" employed alone or in combination with other terms means, unless otherwise stated, an alkyl group or an alkyl group containing a substituent such as a hydroxyl group, having the designated number of carbon atoms connected to the rest of the molecule via an oxygen atom, such as, for example, —OCH(OH)—, —$OCH_2OH$, methoxy (—$OCH_3$), ethoxy (—$OCH_2CH_3$), 1-propoxy (—$OCH_2CH_2CH_3$), 2-propoxy (isopropoxy), butoxy (—$OCH_2CH_2CH_2CH_3$), pentoxy (—$OCH_2CH_2CH_2CH_2CH_3$), and the higher homologs and isomers.

The term "acyl" means a functional group of the general formula —C(=O)—R, wherein —R is hydrogen, alkyl, amino or alkoxy. Examples include acetyl (—C(═O)CH$_3$), propionyl (—C(═O)CH$_2$CH$_3$), benzoyl (—C(═O)C$_6$H$_5$), phenylacetyl (C(═O)CH$_2$C$_6$H$_5$), carboethoxy (—CO$_2$CH$_2$CH$_3$), and dimethylcarbamoyl (C(═O)N(CH$_3$)$_2$).

The terms "halo" or "halogen" by themselves or as part of another substituent mean, unless otherwise stated, a fluorine, chlorine, bromine, or iodine atom.

The term "heterocycle" or "heterocyclyl" or "heterocyclic" by itself or as part of another substituent means, unless otherwise stated, a saturated or unsaturated, stable, mono or multicyclic ring system comprising carbon atoms and at least one heteroatom selected from the group comprising N, O, and S, and wherein the nitrogen and sulfur heteroatoms may be optionally oxidized, and the nitrogen atom may be optionally quaternized. Examples include pyridine, pyrrole, imidazole, benzimidazole, phthalein, pyridenyl, pyranyl, furanyl, thiazole, thiophene, oxazole, pyrazole, 3-pyrroline, pyrrolidene, pyrimidine, purine, quinoline, isoquinoline, carbazole, etc. Where substitution will result in a stable compounds, the structure may be optionally substituted with one or more substituents, independently selected from halogen; (C$_1$-C$_6$)alkyl; (C$_1$-C$_6$)alkenyl; (C$_1$-C$_6$)alkoxy; OH; NO$_2$; C≡N; C(═O)O(C$_1$-C$_3$)alkyl; (C$_2$-C$_6$)alkylene-OR$^2$; phosphonato; NR$^2$$_2$; NHC(═O)(C$_1$-C$_6$)alkyl; sulfamyl; carbamyl; OC(═O)(C$_1$-C$_3$)alkyl; O(C$_2$-C$_6$)alkylene-N((C$_1$-C$_6$)alkyl)$_2$; and (C$_1$-C$_3$)perfluoroalkyl.

The term "amphipathic lipid" means a lipid molecule having a polar end and a non-polar end.

A "complexing agent" is a compound capable of forming a water insoluble coordination complex with a metal, e.g. a salt of chromium, zirconium, etc., that is substantially insoluble in water and soluble in organic solvents.

"Aqueous media" means media comprising water or media comprising water containing at least one buffer or salt.

The terms "associated," or "associated with" when used in reference to a composition or constituent of a composition of the invention, means that the referenced material is incorporated (or intercalated) into, or on the surface of, or within a composition or a constituent of a composition of the present invention.

The term "insulin" refers to natural or recombinant forms of insulin, synthetic insulin, and derivatives of the aforementioned insulins. Examples of insulin include, but are not limited to insulin lispro, insulin aspart, regular insulin, insulin glargine, insulin zinc, human insulin zinc extended, isophane insulin, human buffered regular insulin, insulin glulisine, recombinant human regular insulin, ultralente insulin, humulin, NPH insulin, Levemir, Novolog, and recombinant human insulin isophane. Also included are animal insulins, such as bovine or porcine insulin.

The terms "glargine" and "glargine insulin" both refer to a recombinant human insulin analog which differs from human insulin in that the amino acid asparagine at position A21 is replaced by glycine and two arginines are added to the C-terminus of the B-chain. Chemically, it is 21A-Gly-30Ba-L-Arg-30Bb-L-Arg-human insulin and has the empirical formula C$_{267}$H$_{404}$N$_{72}$O$_{78}$S$_6$ and a molecular weight of 6063.

The term "recombinant human insulin isophane" refers to a human insulin that has been treated with protamine.

The term "bioavailability" refers to a measurement of the rate and extent that a pharmaceutical agent, such as, but not limited to, insulin, reaches the systemic circulation and is available at its site of action.

As used herein, to "treat" means reducing the frequency with which symptoms of a disease, disorder, or adverse condition, and the like, are experienced by a patient.

As used herein, the term "pharmaceutically acceptable carrier" means a chemical composition with which the active ingredient may be combined and which, following the combination, can be used to administer the active ingredient to a subject.

The term "lipid" or "lipids" means an organic compound characterized by its preference for non-polar aprotic organic solvents. A lipid may or may not possess an alkyl tail. Lipids according to the present invention include, but are not limited to, the class of compounds known in the art as phospholipids, cholesterols, and dialkyl phosphates.

As used herein, "cholesterol" means the compound and all derivatives and analogs of the compound:

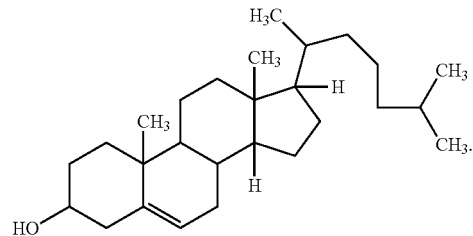 [SMILES: CC(C)CCCC(C)C1CCC2C3CC=C4CC(O)CCC4(C)C3CCC12C]

As used herein, "particle" comprises an agglomeration of multiple units of one or more lipids.

As used herein, "thyroxine" refers to the compound:

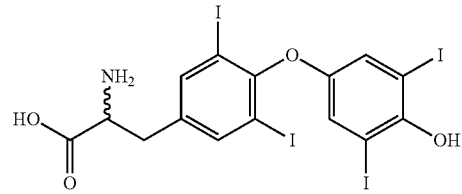 [SMILES: NC(Cc1cc(I)c(Oc2cc(I)c(O)c(I)c2)c(I)c1)C(=O)O]

wherein the amino group may be in either the "D" or "L" configuration.

As used herein, "co-administration" or "co-administering" or "co-administered" as well as variations thereof, mean administering a composition of the invention before, during, or after the administration of one or more additional therapeutic agents wherein the one or more additional therapeutic agents is/are not associated with the composition of the invention. Co-administration may take place via the same or different routes of administration. Co-administration may be concurrent, sequential, or spaced at specific time intervals. Co-administration need not, however, take place within a set time period. As such, and by way of example only, administration of a composition of the invention at any time before or after the administration of one or more additional therapeutic agents constitutes co-administration so long as either a composition of the invention or the one or more additional therapeutics (whichever is administered first) is still present in the patient at the time of co-administration. In certain embodiments, though, the first administered compound need not be present in the patient at the time of co-administration.

As used herein, "interferon" refers to all forms of interferon, including, but not limited to, interferon-α, interferon-beta, interferon-gamma, as well as sub-units thereof.

DESCRIPTION

A composition of the present invention is comprised of gelatin and one or more constituents wherein said constituents include liposomes, liposome fragments, and lipid particles.

Traditionally, liposome, liposome fragments, and lipid particles comprised of amphipathic materials have been limited to a lower size distribution of about 40 nanometers. This limit was believed to be a function of the collective sizes of the constituent lipids (phospholipids, cholesterols, dialkylphosphates, etc.) that constituted the membrane structure.

The constituents of a composition of the present invention, however, demonstrate heretofore unobserved dynamic sizing and size elasticity. Specifically, constituents of the compositions of the present invention, exist in a dynamic equilibrium in aqueous media wherein the constituents, on average, fluctuate in size from about 6 nanometers to about 60 nanometers in diameter. At any given time, anywhere from about 5% to about 50% of the constituents exhibit an average diameter of about 20 nanometers or less. Due to the nearly constant fluctuations in sizes, the constituents of the compositions of the present invention cannot be physically separated by traditional fractionating means to form discrete populations of differently sized structures. The constituents of a composition of the invention may be, but are not limited to, a liposome, a liposome fragment, and a lipid particle. The composition of the invention can further optionally include a targeting agent.

Lipids

A constituent of a composition of the present invention comprises one or more lipid components and an optional targeting agent. An embodiment comprising a single unit or multiple units of a single lipid component is referred to herein as a "lipid particle." An embodiment comprising two or more different lipid components and an optional targeting agent is classified as a liposome or liposome fragment, depending upon the nature of the resulting structure.

Lipid components of the present invention are selected from the group consisting of 1,2-distearoyl-sn-glycero-3-phosphocholine, 1,2-dipalmitoyl-sn-glycero-3-phosphocholine, 1,2-dimyristoyl-sn-glycero-3-phosphocholine, cholesterol, cholesterol oleate, dihexadecyl phosphate, 1,2-distearoyl-sn-glycero-3-phosphate, 1,2-dipalmitoyl-sn-glycero-3-phosphate, 1,2-dimyristoyl-sn-glycero-3-phosphate, 1,2-distearoyl-sn-glycero-3-phosphoethanolamine, 1,2-dipalmitoyl-sn-glycero-3-phosphoethanolamine-N-(succinyl), 1,2-dipalmitoyl-sn-glycero-3-[phospho-rac-(1-glycerol)] (sodium salt), triethylammonium 2,3-diacetoxypropyl 2-(5-((3aS,6aR)-2-oxohexahydro-1H-thieno[3,4-d]imidazol-4-yl) pentanamido)ethyl phosphate, MPB-PE and derivatives thereof. Representative structures are presented in Table 1.

TABLE 1

| Common Name | Chemical Name | Structure |
|---|---|---|
| 1,2-distearoyl-sn-glycero-3-phosphocholine | 2,3-bis(stearoyloxy)propyl 2-(trimethylammonio)ethyl phosphate | 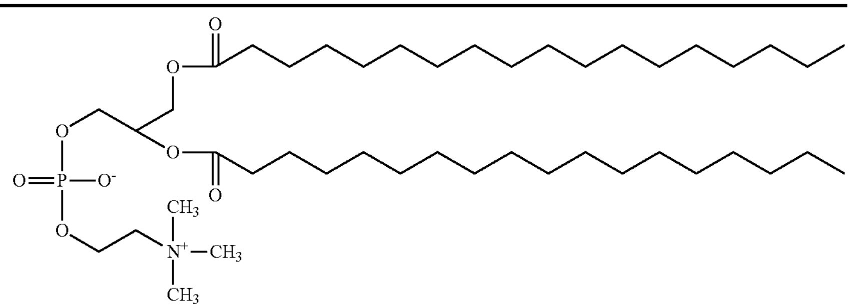 |
| 1,2-dipalmitoyl-sn-glycero-3-phosphocholine | 2,3-bis(palmitoyloxy)propyl 2-(trimethylammonio)ethyl phosphate | 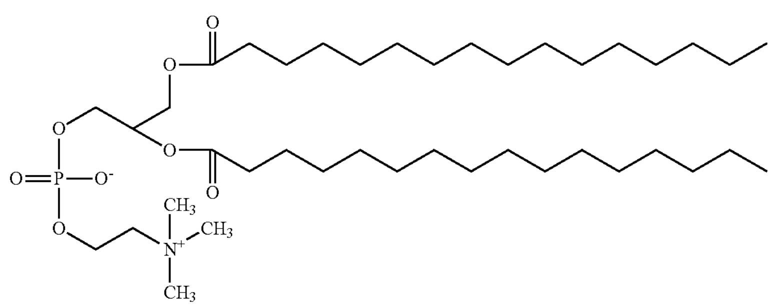 [SMILES: CCCCCCCCCCCCCCCC(=O)OCC(COP(=O)([O-])OCC[N+](C)(C)C)OC(=O)CCCCCCCCCCCCCCC] |
| 1,2-dimyristoyl-sn-glycero-3-phosphocholine | 2,3-bis(tetradecanoyloxy)propyl 2-(trimethylammonio)ethyl phosphate | 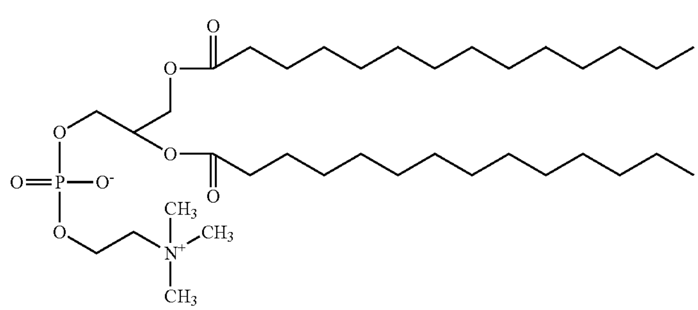 [SMILES: CCCCCCCCCCCCCC(=O)OCC(COP(=O)([O-])OCC[N+](C)(C)C)OC(=O)CCCCCCCCCCCCC] |

TABLE 1-continued

| Common Name | Chemical Name | Structure |
|---|---|---|
| Cholesterol | 10,13-dimethyl-17-(6-methylheptan-2-yl)-2,3,4,7,8,9,10,11,12,13,14,15,16,17-tetradecahydro-1H-cyclopenta[a]phenanthren-3-ol | 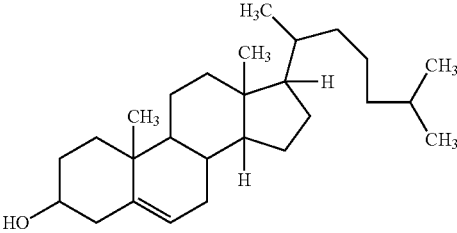 [SMILES: CC(C)CCCC(C)C1CCC2C3CC=C4CC(O)CCC4(C)C3CCC12C] |
| MPB-PE | | 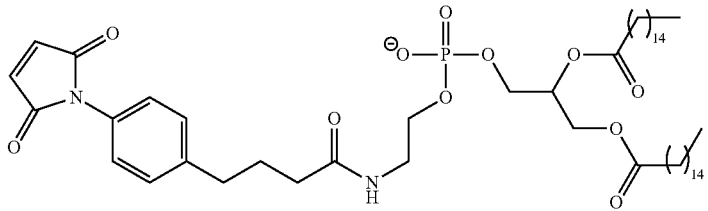 |

By way of non-limiting examples, the constituents of a composition of the present invention may be formed from lipid components mixed in accordance with the following: approximately 61 mole percent 1,2 distearoyl-sn-glycero-3-phosphocholine, approximately 22 mole percent dihexadecyl phosphate, and approximately 16 mole percent cholesterol. In embodiments wherein a constituent incorporates a targeting agent, the above noted mixture may further include from about 1 to about 2 mole percent of at least one targeting agent, with the amounts of other lipid components reduced to maintain the ratio of components set forth above.

In another embodiment, a composition of the present invention may be formed from lipid components mixed in accordance with the following: approximately 68 mole percent 1,2 dipalmitoyl-sn-glycero-3-phosphocholine, approximately 18 mole percent dihexadecyl phosphate, approximately 9 mole percent cholesterol, and approximately 3 percent MPB-PE. In embodiments wherein a constituent incorporates a targeting agent, the above noted mixture may further include from about 1 to about 2 mole percent of at least one targeting agent, with the amounts of other lipid components reduced to maintain the ratio of components set forth above.

Preparation

Generally, the constituents of a composition of the present invention are formed when at least one lipid component and optional targeting agent are homogenized in an aqueous media via microfluidization or other process involving cavitation.

In an embodiment of the invention, the lipid component(s) and optional targeting agent(s) may be homogenized in 18 mM phosphate buffer at a pH of about 6.0 to a pH of about 8.0. Lipid component concentration in the phosphate buffer may range from about 10 to about 200 mg/ml and any and all whole and partial integers therebetween. In one embodiment, the lipid component concentration is about 30 to about 150 mg/ml. In more preferred embodiment, the lipid component concentration is about 15 to about 50 mg/ml. In a most preferred embodiment, the lipid component concentration is about 28-30 mg/ml.

Homogenization of the aqueous media, lipid component(s), and optional targeting agent may be accomplished via treatment in a device suitable for homogenization. Examples of suitable devices include, but are not limited to, a Polytron® System PT 6100, an M-110-EH microfluidizer, an ultrasonic sonicator, a high pressure membrane filtration apparatus, and a homogenizer extruder.

In instances where a microfluidizer is used, the microfluidizer is preferably operated at a temperature that is greater than the highest transition temperature of a lipid component and most preferably at a temperature greater than about 75° C. Thus, the elevated temperature allows any acyl and alkyl chains present in the lipid component(s) to move fluidly as well as conform to and associate with neighboring hydrocarbon moieties. These non-covalent associations directly result in the formation of a constituent of a composition of the present invention.

Figure 9:
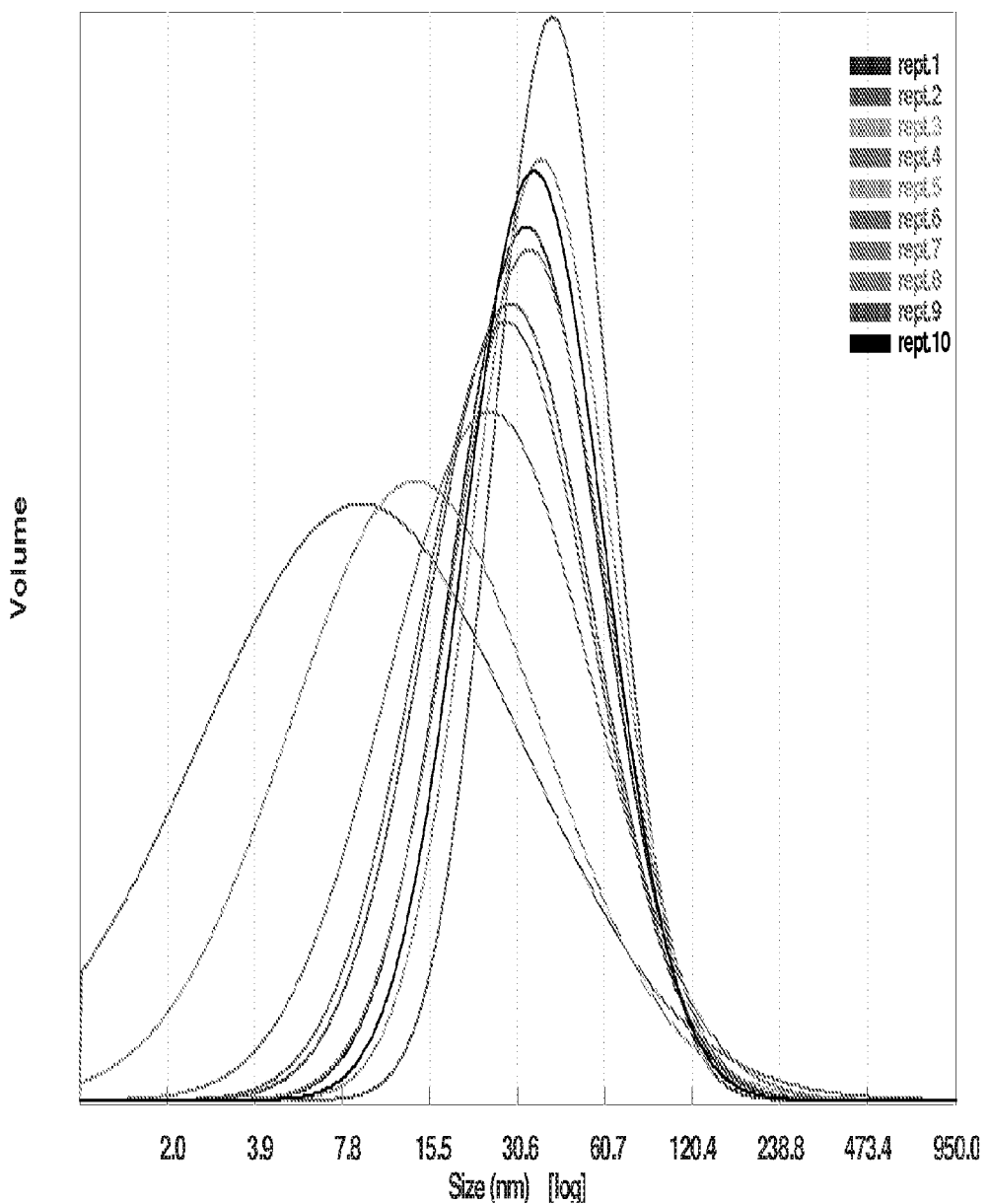
FIG. 9 is a graph of the size distribution of the constituent members of a composition of the invention.

For the microfluidization process, up to about five independent passes are required at 9000 psig in order to achieve dynamic constituent sizing with some constituents possessing radii of less than 20 nanometers. Constituent analysis data generated by a Coulter N-4 Plus Sub-Micron Particle Size Analyzer is shown in FIG. 9 and represents 10 repeated size analyses on the same sample as it remained stationary in the Coulter N-4 Plus Sub-Micron Particle Size Analyzer. This data demonstrates the dynamic nature of constituent sizing and the fluid nature of the interactions between the constituents of the composition of the present invention in aqueous media.

After microfluidization, the resulting constituents may be sterile filtered through a 0.8 micron to 0.2 micron gang Supor™ membrane.

During the process of sub-micron particle formation, hydrogen bonding, ionic bonding, van der Waal's interactions, dipolar interactions, ion-dipole interactions and hydrophobic associations dictate the manner in which the constituents of a composition of the present invention assemble. While not wishing to be bound by any one particular theory, it is believed that the interaction of all of these forces, to varying extents, under the conditions noted above, lead to the dynamically sized constituents of the present invention.

Incorporation of a Targeting Agent

In certain embodiments, a constituent of the present invention may optionally comprise a targeting agent. Targeting agents alter a constituent's bio-distribution and further enhance the efficacy of an associated therapeutic agent. For example, a constituent of a composition of the present invention may incorporate one or more targeting agents that act to target the constituent to a specific cellular or extracellular receptor. Alternatively, by way of a non-limiting example, the targeting agent may mask the constituent from reticuloendothelial (macrophage) recognition.

In one embodiment, a targeting agent facilitates delivery of the composition to the liver and encompasses a class of molecules referred to as "hepatocyte target molecule" (HTM). HTM examples include biotin derived targeting agents such as 1,2-dipalmitoyl-sn-glycero-3-phosphoethanolamine-N-(biotinyl) and metal derived targeting agents such as poly[Cr-bis(N-2,6-diisopropylphenylcarbamoylmethyl iminodiacetic acid)]. Metal-derived targeting agents and biotin derived targeting agents are discussed below and are fully described in U.S. Pat. Nos. 7,169,410 and 4,603,044; PCT application PCT/US06/19119; and U.S. patent application Ser. Nos. 11/384,728, and 11/384,659. Additional examples of biotin-derived targeting agents are disclosed in Table 2.

When the targeting agent comprises biotin, iminobiotin, carboxybiotin, biocytin, or iminobiocytin, the biotin, iminobiotin, carboxybiotin, biocytin, or iminobiocytin molecules may be bound via an amide bond to the nitrogen of a phospholipid molecule such as 1,2-dipalmitoyl-sn-glycero-3-phosphoethanolamine. The compounds may likewise be bound to a molecule such as cholesterol through an ester linkage. In the case of biocytin and iminobiocytin, the compounds may be bound to benzoyl thioacetyl triglycine via an amide bond between the terminal nitrogen of iminobiocytin and the terminal carbonyl of benzoyl thioacetyl triglycine. Alternative bond connectivities to those described above are possible and considered to be within the scope of the present invention.

TABLE 2

| | | |
|---|---|---|
| 1 | N-hydroxy-succinimide (NHS) biotin 2,5-dioxo-pyrrolidin-1-yl 5-((3aS,6aR)-2-oxohexahydro-1H-thieno[3,4-d]imidazol-4-yl)pentanoate | 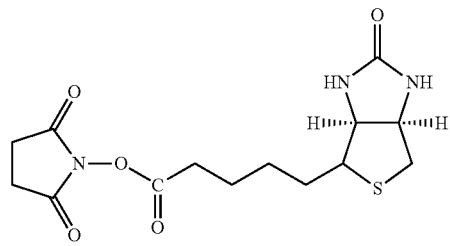 [SMILES: O=C1N[C@H]2CSC(CCCCC(=O)ON3C(=O)CCC3=O)[C@H]2N1] |
| 2 | sulfo-NHS-biotin sodium 2,5-dioxo-3-(trioxidanylthio)pyrrolidin-1-yl 5-((3aS,6aR)-2-oxo-hexahydro-1H-thieno[3,4-d]imidazol-4-yl)pentanoate | 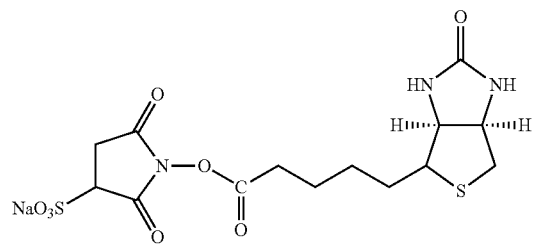 |
| 3 | N-hydroxysuccinimide long chain biotin 2,5-dioxopyrrolidin-1-yl 6-(5-((3aS,6aR)-2-oxohexahydro-1H-thieno[3,4-d]imidazol-4-yl)pentanamido)hexanoate | 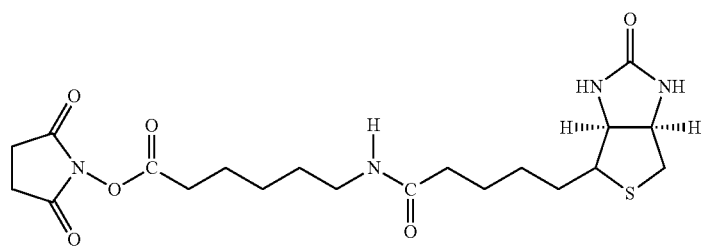 [SMILES: O=C(CCCCC1SC[C@@H]2NC(=O)N[C@H]12)NCCCCCC(=O)ON1C(=O)CCC1=O] |
| 4 | sulfo-N-hydroxy-succinimide long chain biotin sodium 2,5-dioxo-3-(trioxidanylthio)pyrrolidin-1-yl 6-(5-((3aS,6aR)-2-oxohexahydro-1H-thieno[3,4-d]imidazol-4-yl)pentanamido)hexanoate | 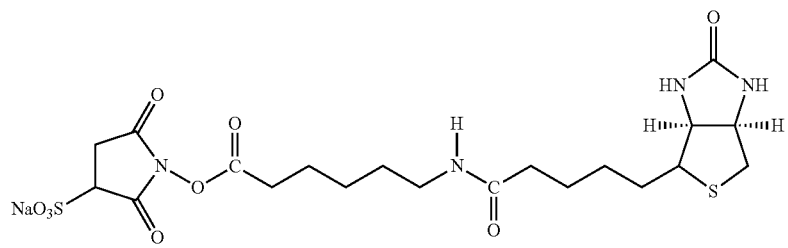 |

TABLE 2-continued

| 5 | D-biotin 5-((3aS,6aR)-2-oxohexahydro-1H-thieno[3,4-d]imidazol-4-yl)pentanoic acid | 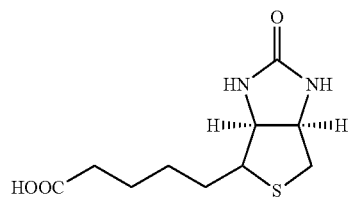 [SMILES: O=C(O)CCCCC1SC[C@@H]2NC(=O)N[C@H]12] |
| --- | --- | --- |
| 6 | Biocytin 2-amino-6-(5-((3aS,6aR)-2-oxohexahydro-1H-thieno[3,4-d]imidazol-4-yl)pentanamido)hexanoic acid | 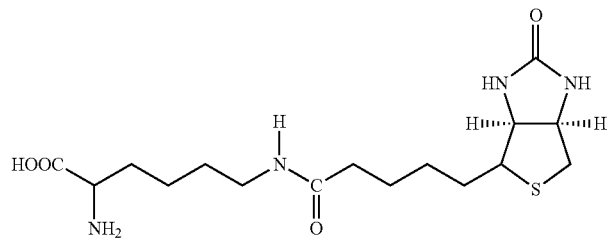 [SMILES: NC(CCCCNC(=O)CCCCC1SC[C@@H]2NC(=O)N[C@H]12)C(=O)O] |
| 7 | sulfo-N-hydroxy-succinimide-S-S-biotin sodium 2,5-dioxo-3-(trioxidanylthio)pyrrolidin-1-yl 3-((2-(4-((3aS,6aR)-2-oxohexahydro-1H-thieno[3,4-d]imidazol-4-yl)butyl-amino)ethyl)disulfanyl)propanoate | 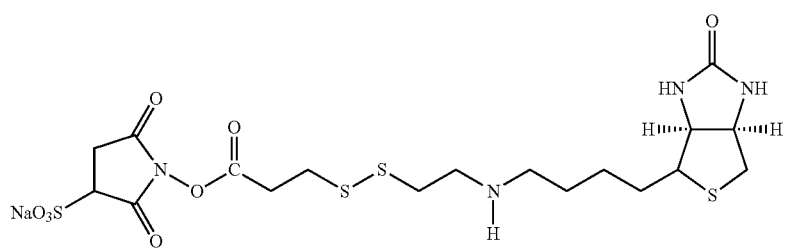 |
| 8 | biotin-BMCC 4-((2,5-dioxo-2,5-dihydro-1H-pyrrol-1-yl)methyl)-N-(4-(5-((3aS,6aR)-2-oxohexahydro-1H-thieno[3,4-d]imidazol-4-yl)pentanamido)butyl)cyclohexane-carboxamide | 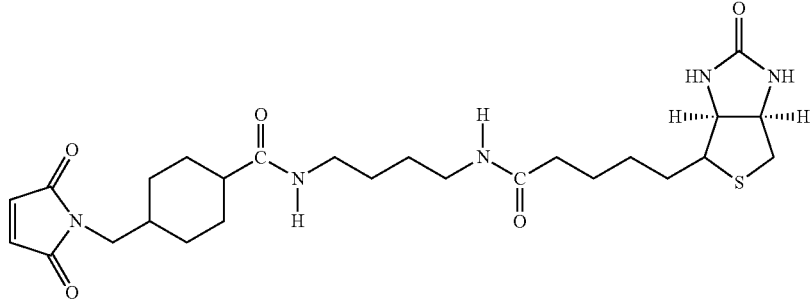 [SMILES: O=C(CCCCC1SC[C@@H]2NC(=O)N[C@H]12)NCCCCNC(=O)C1CCC(CN2C(=O)C=CC2=O)CC1] |
| 9 | biotin-HPDP 5-((3aS,6aR)-2-oxo-hexahydro-1H-thieno[3,4-d]imidazol-4-yl)-N-(6-(3-(pyridin-2-yldisulfanyl)propanamido)hexyl)pentanamide | 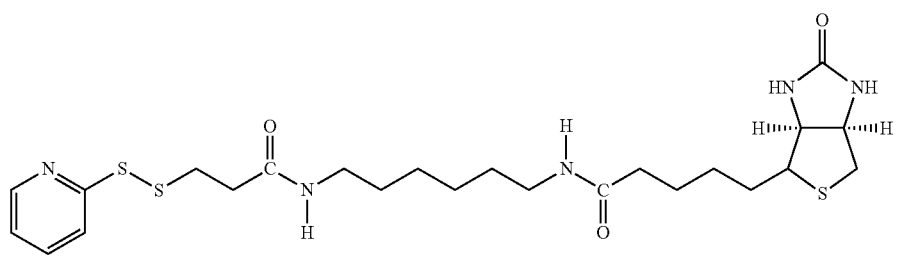 [SMILES: O=C(CCCCC1SC[C@@H]2NC(=O)N[C@H]12)NCCCCCCNC(=O)CCSSc1ccccn1] |
| 10 | iodoacetyl-LC-biotin N-(6-(2-iodoacetamido)hexyl)-5-((3aS,6aR)-2-oxohexa-hydro-1H-thieno[3,4-d]imidazol-4-yl)pentanamide | 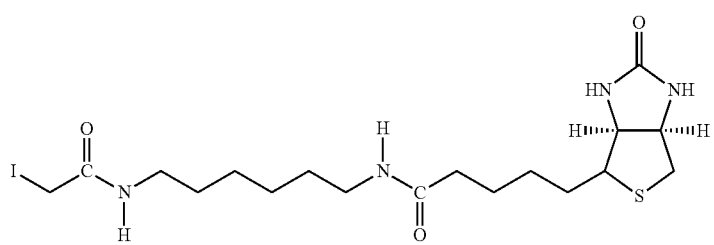 [SMILES: O=C(CI)NCCCCCCNC(=O)CCCCC1SC[C@@H]2NC(=O)N[C@H]12] |

TABLE 2-continued

| 11 | biotin-hydrazide 5-((3aS,6aR)-2-oxo-hexahydro-1H-thieno[3,4-d]imidazol-4-yl)pentanehydrazide | 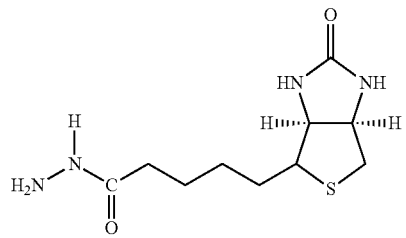 [SMILES: NNC(=O)CCCCC1SC[C@@H]2NC(=O)N[C@H]12] |
| --- | --- | --- |
| 12 | biotin-LC-hydrazide N-(6-hydrazinyl-6-oxo-hexyl)-5-((3aS,6aR)-2-oxohexahydro-1H-thieno[3,4-d]imidazol-4-yl)pentanamide | 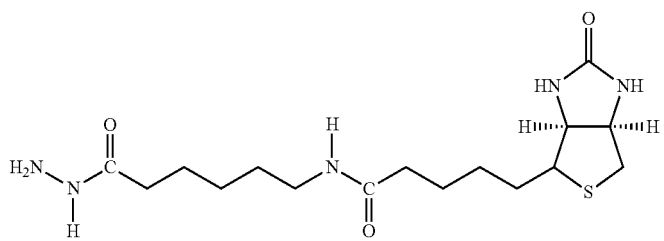 [SMILES: NNC(=O)CCCCCNC(=O)CCCCC1SC[C@@H]2NC(=O)N[C@H]12] |
| 13 | biocytin hydrazide N-(5-amino-6-hydrazinyl-6-oxohexyl)-5-((3aS,6aR)-2-oxohexahydro-1H-thieno[3,4-d]imidazol-4-yl)pentanamide | 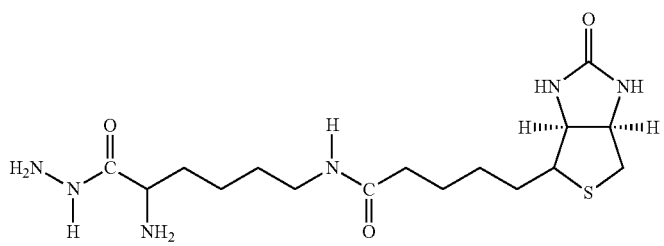 [SMILES: NNC(=O)C(N)CCCCNC(=O)CCCCC1SC[C@@H]2NC(=O)N[C@H]12] |
| 14 | biotin cadaverine N-(5-aminopentyl)-5-((3aS,6aR)-2-oxohexahydro-1H-thieno[3,4-d]imidazol-4-yl)pentanamide | 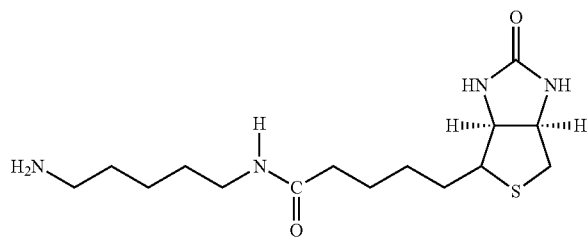 [SMILES: NCCCCCNC(=O)CCCCC1SC[C@@H]2NC(=O)N[C@H]12] |
| 15 | Carboxybiotin (3aS,6aR)-4-(4-carboxybutyl)-2-oxohexahydro-1H-thieno[3,4-d]imidazole-1-carboxylic acid | 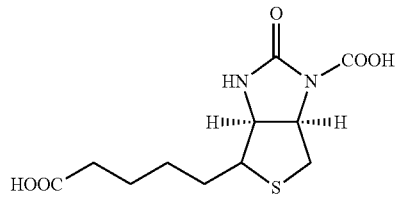 [SMILES: O=C(O)CCCCC1SC[C@H]2[C@@H]1NC(=O)N2C(=O)O] |
| 16 | Photobiotin N-(3-((3-(4-azido-2-nitrophenylamino)propyl)(methyl)amino)propyl)-5-((3aS,6aR)-2-oxohexahydro-1H-thieno[3,4-d]imidazol-4-yl)pentanamide | 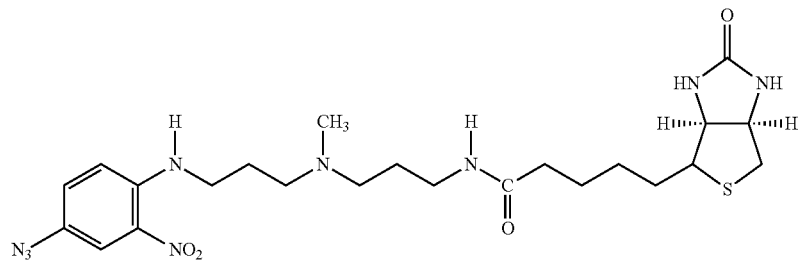 [SMILES: CN(CCCNC(=O)CCCCC1SC[C@@H]2NC(=O)N[C@H]12)CCCNc1ccc(N=[N+]=[N-])cc1[N+](=O)[O-]] |

TABLE 2-continued

| 17 | p-aminobenzoyl biocytin trifluoroacetate<br>2-(4-aminobenzamido)-6-(5-((3aS,6aR)-2-oxohexahydro-1H-thieno[3,4-d]imidazol-4-yl)pentanamido)hexanoic acid 2,2,2-trifluoroacetate | 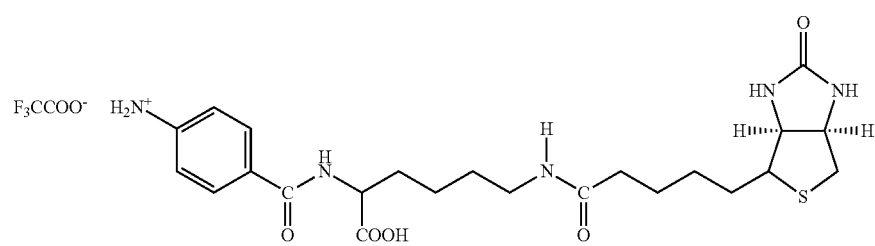 [SMILES: "F3CCOO-" ; [NH3+]c1ccc(C(=O)NC(CCCCNC(=O)CCCCC2SC[C@@H]3NC(=O)N[C@H]23)C(=O)O)cc1] |
| --- | --- | --- |
| 18 | p-diazobenzoyl biocytin<br>4-(1-carboxy-5-(5-((3aS,6aR)-2-oxohexahydro-1H-thieno[3,4-d]imidazol-4-yl)pentanamido)pentylcarbamoyl)benzenediazonium chloride | 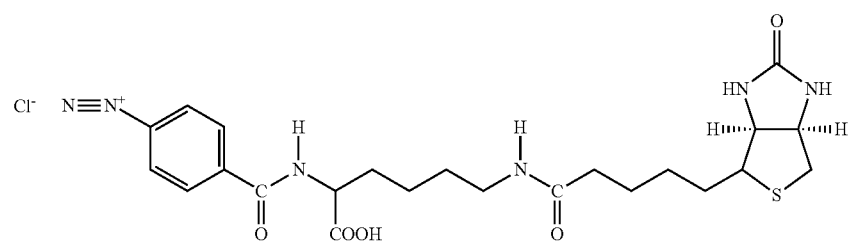 [SMILES: [Cl-] ; N#[N+]c1ccc(C(=O)NC(CCCCNC(=O)CCCCC2SC[C@@H]3NC(=O)N[C@H]23)C(=O)O)cc1] |
| 19 | biotin DHPE<br>$G^+$ = $Li^+$, $Na^+$, $K^+$, $(Et_3NH)^+$<br>2,3-diacetoxypropyl 2-(5-((3aS,6aR)-2-oxo-hexahydro-1H-thieno[3,4-d]imidazol-4-yl)pentanamido)ethyl phosphate | 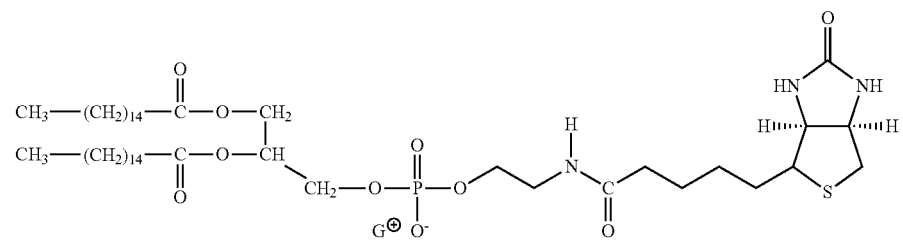 |
| 20 | biotin-X—DHPE<br>$G^+$ = $Li^+$, $Na^+$, $K^+$, $(Et_3NH)^+$<br>2,3-diacetoxypropyl 2-(6-(5-((3aS,6aR)-2-oxohexahydro-1H-thieno[3,4-d]imidazol-4-yl)pentanamido)hexanamido)ethyl phosphate | 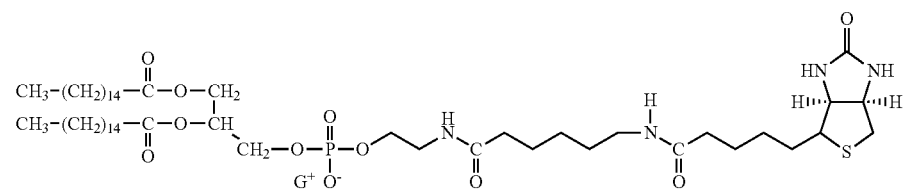 |
| 21 | 12-((biotinyl)amino)dodecanoic acid<br>12-(5-((3aS,6aR)-2-oxohexahydro-1H-thieno[3,4-d]imidazol-4-yl)pentanamido)dodecanoic acid | 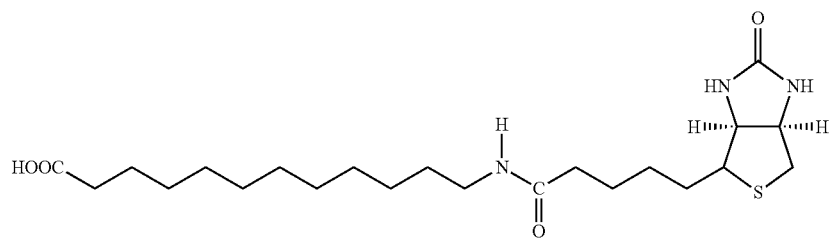 [SMILES: O=C(O)CCCCCCCCCCCNC(=O)CCCCC1SC[C@@H]2NC(=O)N[C@H]12] |
| 22 | 12-((biotinyl)amino)dodecanoic acid succinimidyl ester<br>2,5-dioxopyrrolidin-1-yl 12-(5-((3aS,6aR)-2-oxohexahydro-1H-thieno[3,4-d]imidazol-4-yl)pentanamido)dodecanoate | 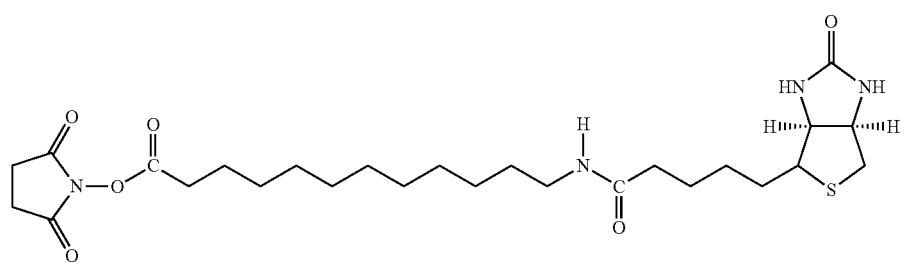 [SMILES: O=C(CCCCC1SC[C@@H]2NC(=O)N[C@H]12)NCCCCCCCCCCCC(=O)ON1C(=O)CCC1=O] |

TABLE 2-continued

| 23 | S-biotinyl homocysteine 4-mercapto-2-(5-((3aS, 6aR)-2-oxohexahydro-1H-thieno[3,4-d]imidazol-4-yl)pentanamido)butanoic acid | 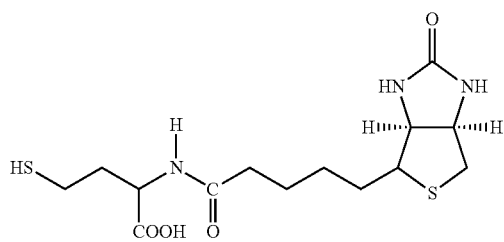 [SMILES: O=C(CCCCC1SC[C@@H]2NC(=O)N[C@H]12)NC(CCS)C(=O)O] |
| --- | --- | --- |
| 24 | biocytin-X 2-amino-6-(6-(5-((3aS,6aR)-2-oxohexahydro-1H-thieno[3,4-d]imidazol-4-yl)pentanamido)hexanamido)hexanoic acid | 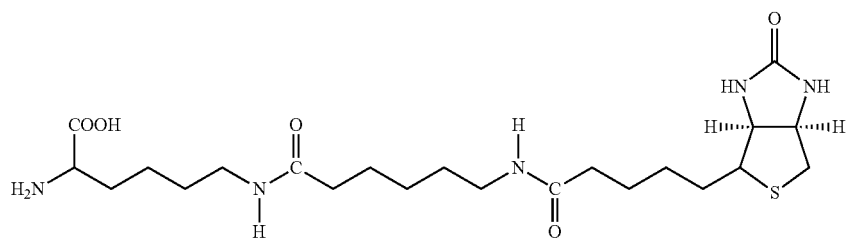 [SMILES: NC(CCCCNC(=O)CCCCCNC(=O)CCCCC1SC[C@@H]2NC(=O)N[C@H]12)C(=O)O] |
| 25 | biocytin x-hydrazide N-(5-amino-6-hydrazinyl-6-oxohexyl)-6-(5-((3aS,6aR)-2-oxohexahydro-1H-thieno[3,4-d]imidazol-4-yl)pentanamido)hexanamide | 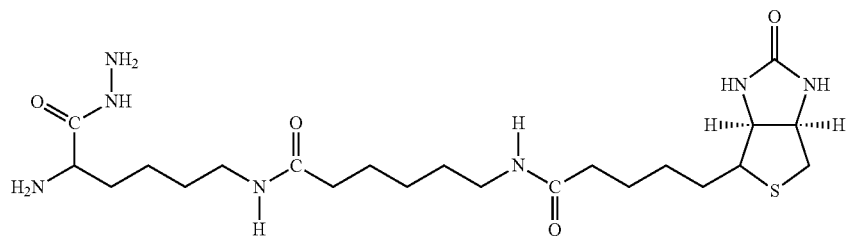 [SMILES: NNC(=O)C(N)CCCCNC(=O)CCCCCNC(=O)CCCCC1SC[C@@H]2NC(=O)N[C@H]12] |
| 26 | Biotinethylenediamine N-(2-aminoethyl)-5-((3aS,6aR)-2-oxohexahydro-1H-thieno[3,4-d]imidazol-4-yl)pentanamide | 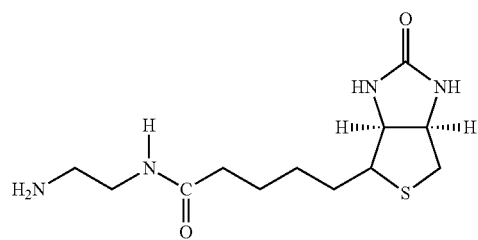 [SMILES: NCCNC(=O)CCCCC1SC[C@@H]2NC(=O)N[C@H]12] |
| 27 | biotin-X 6-(5-((3aS,6aR)-2-oxohexahydro-1H-thieno[3,4-d]imidazol-4-yl)pentanamido)hexanoic acid | 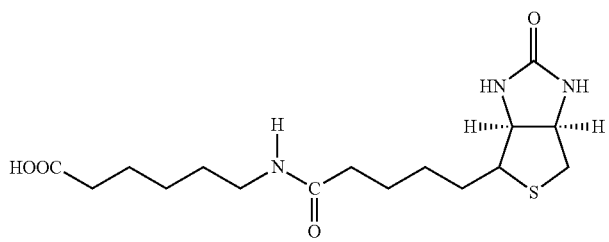 [SMILES: O=C(O)CCCCCNC(=O)CCCCC1SC[C@@H]2NC(=O)N[C@H]12] |
| 28 | biotin-X-ethylenediamine N-(2-aminoethyl)-6-(5-((3aS,6aR)-2-oxohexahydro-1H-thieno[3,4-d]imidazol-4-yl)pentanamido)hexanamide | 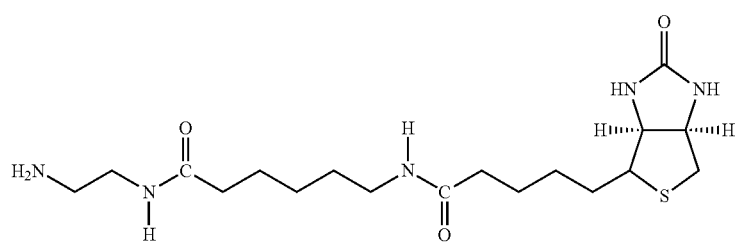 [SMILES: NCCNC(=O)CCCCCNC(=O)CCCCC1SC[C@@H]2NC(=O)N[C@H]12] |

TABLE 2-continued

| 29 | biotin-XX hydrazide N-(6-hydrazinyl-6-oxo-hexyl)-6-(5-((3aS,6aR)-2-oxohexahydro-1H-thieno[3,4-d]imidazol-4-yl)pentanamido)hexanamide | 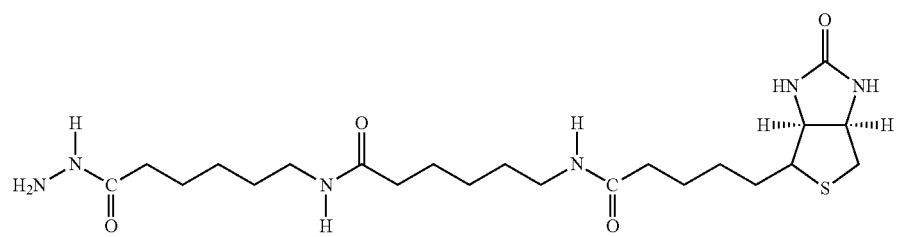 [SMILES: NNC(=O)CCCCCNC(=O)CCCCCNC(=O)CCCCC1SC[C@@H]2NC(=O)N[C@H]12] |
| --- | --- | --- |
| 30 | biotin-XX-SE 1,5-dioxopyrrolidin-1-yl 6-(6-(5-((3aS,6aR)-2-oxohexahydro-1H-thieno[3,4-d]imidazol-4-yl)pentanamido)hexanamido)hexanoate | 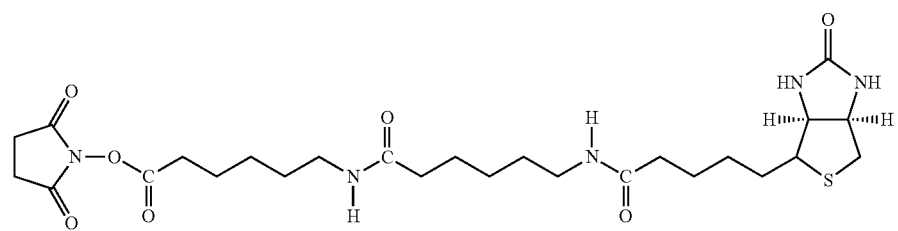 [SMILES: O=C(CCCCCNC(=O)CCCCC1SC[C@@H]2NC(=O)N[C@H]12)NCCCCCC(=O)ON1C(=O)CCC1=O] |
| 31 | biotin-XX,SSE sodium 2,5-dioxo-1-(6-(6-(5-((3aS,6aR)-2-oxohexahydro-1H-thieno[3,4-d]imidazol-4-yl)pentanamido)hexanamido)hexanoyloxy)pyrrolidine-3-sulfonate | 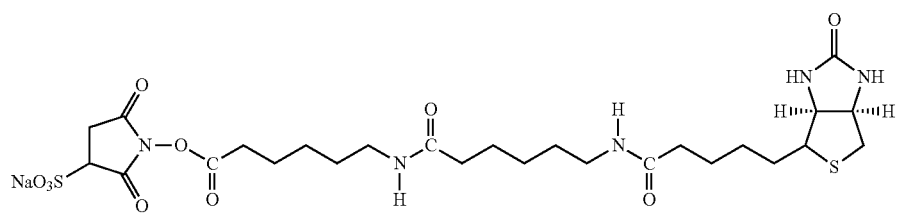 |
| 32 | biotin-X-cadaverine 5-(6-(5-((3aS,6aR)-2-oxohexahydro-1H-thieno[3,4-d]imidazol-4-yl)pentanamido)hexanamido)pentan-1-aminium 2,2,2-trifluoroacetate | 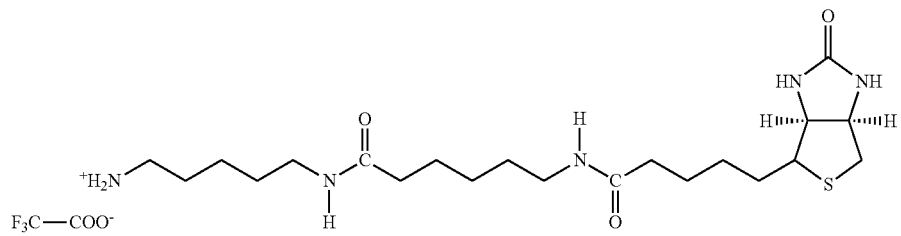 |
| 33 | α-(t-BOC)biocytin 2-(tert-butoxy-carbonylamino)-6-(5-((3aS,6aR)-2-oxohexahydro-1H-thieno[3,4-d]imidazol-4-yl)pentanamido)hexanoic acid | 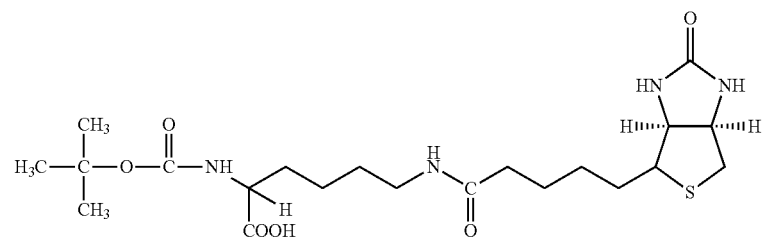 [SMILES: CC(C)(C)OC(=O)NC(CCCCNC(=O)CCCCC1SC[C@@H]2NC(=O)N[C@H]12)C(=O)O] |
| 34 | N-(biotinyl)-N'-(iodoacetyl)ethylenediamine N-(2-(2-iodoacetamido)ethyl)-5-((3aS,6aR)-2-oxohexahydro-1H-thieno[3,4-d]imidazol-4-yl)pentanamide | 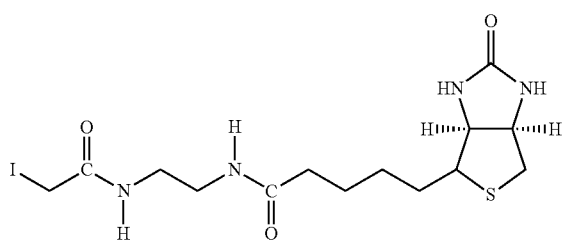 [SMILES: O=C(CI)NCCNC(=O)CCCCC1SC[C@@H]2NC(=O)N[C@H]12] |

TABLE 2-continued

| | | |
|---|---|---|
| 35 | DNP-X-biocytin-X-SE 2,5-dioxopyrrolidin-1-yl 2-(6-(6-(2,4-dinitrophenylamino)hexanamido)hexanamido)-6-(6-(5-((3aS,6aR)-2-oxohexahydro-1H-thieno[3,4-d]imidazol-4-yl)pentanamido)hexanamido)hexanoate | 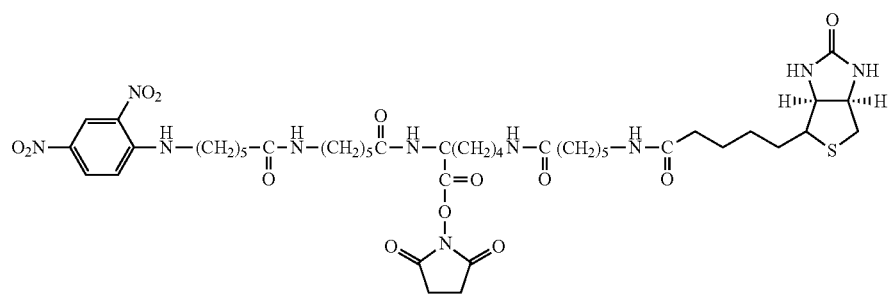 |
| 36 | biotin-X-hydrazide N-(6-hydrazinyl-6-oxohexyl)-5-((3aS,6aR)-2-oxohexahydro-1H-thieno[3,4-d]imidazol-4-yl)pentanamide | 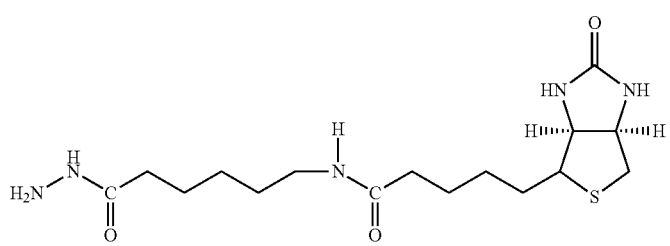 [SMILES: NNC(=O)CCCCCNC(=O)CCCCC1SC[C@@H]2NC(=O)N[C@H]12] |
| 37 | norbiotinamine hydrochloride 4-((3aS,6aR)-2-oxohexahydro-1H-thieno[3,4-d]imidazol-4-yl)butan-1-aminium chloride | 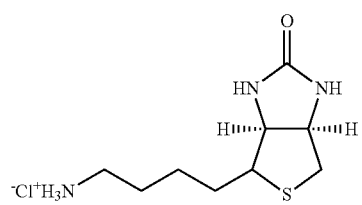 |
| 38 | 3-(N-maleimidylpropionyl)biocytin 2-(3-(2,5-dioxo-2,5-dihydro-1H-pyrrol-1-yl)propanamido)-6-(5-(3aS,6aR)-2-oxohexahydro-1H-thieno[3,4-d]imidazol-4-yl)pentanamido)hexanoic acid | 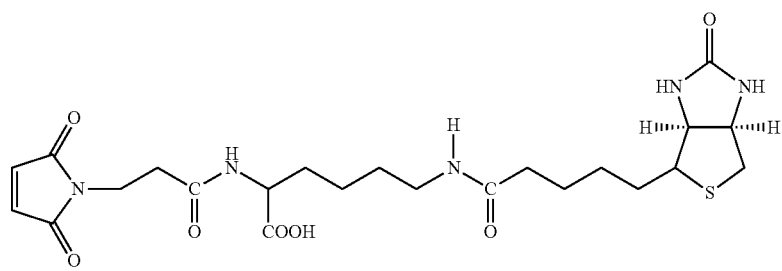 [SMILES: O=C(CCCCC1SC[C@@H]2NC(=O)N[C@H]12)NCCCCC(NC(=O)CCN1C(=O)C=CC1=O)C(=O)O] |
| 39 | ARP; N'-(2-(aminooxy)acetyl)-5-((3aS,6aR)-2-oxohexahydro-1H-thieno[3,4-d]imidazol-4-yl)pentanehydrazide | 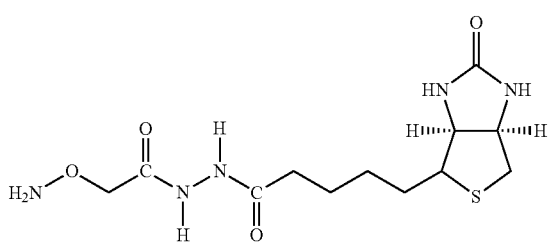 [SMILES: NOCC(=O)NNC(=O)CCCCC1SC[C@@H]2NC(=O)N[C@H]12] |
| 40 | biotin-1-sulfoxide 5-((3aS,6aR)-2-oxohexahydro-1H-thieno[3,4-d]imidazol-4-yl)pentanoic acid sulfoxide | 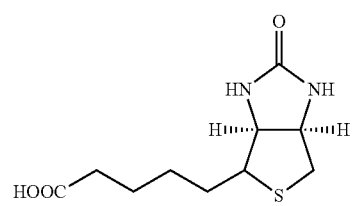 [SMILES: O=C(O)CCCCC1SC[C@@H]2NC(=O)N[C@H]12] |

TABLE 2-continued

| 41 | biotin methyl ester methyl 5-((3aS,6aR)-2-oxohexahydro-1H-thieno[3,4-d]imidazol-4-yl)pentanoate | 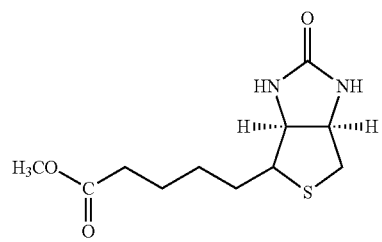 [SMILES: COC(=O)CCCCC1SC[C@@H]2NC(=O)N[C@H]12] |
| --- | --- | --- |
| 42 | biotin-maleimide 6-(2,5-dioxo-2,5-dihydro-1H-pyrrol-1-yl)-N'-(5-((3aS,6aR)-2-oxohexahydro-1H-thieno[3,4-d]imidazol-4-yl)pentanoyl)hexanehydrazide | 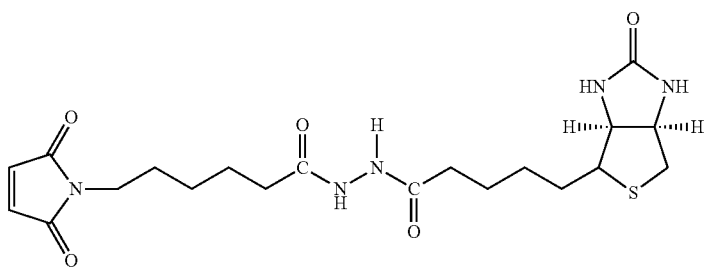 [SMILES: O=C(CCCCCN1C(=O)C=CC1=O)NNC(=O)CCCCC1SC[C@@H]2NC(=O)N[C@H]12] |
| 43 | Biotin-poly(ethyleneglycol)amine aminomethyl polyethylene 5-((3aS,6aR)-2-oxohexahydro-1H-thieno[3,4-d]imidazol-4-yl)pentanoate | 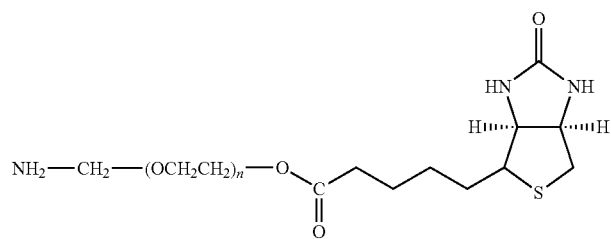 |
| 44 | (+) biotin 4-amidobenzoic acid sodium salt sodium 4-(50((3aS,6aR)-2-oxohexahydro-1H-thieno[3,4-d]imidazol-4-yl)pentaamido)benzoate | 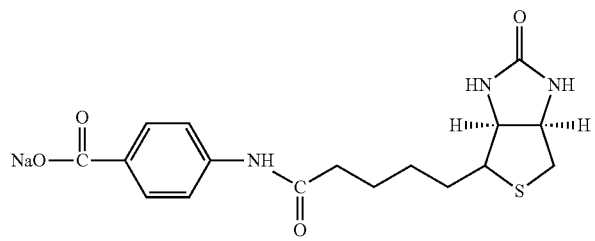 |
| 45 | Biotin 2-N-acetylamino-2-deoxy-β-D-glucopyranoside ((2R,5S)-3-acetamido-4,5-dihydroxy-6-(hydroxymethyl)-2,3,4,6-penta-methyltetrahydro-2H-pyran-2-yl)methy 5-((3aS,6aR)-2-oxohexahydro-1H-thieno[3,4-d]imidazol-4-yl)pentanoate | 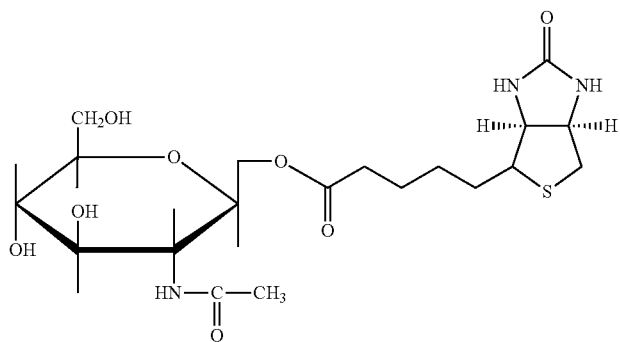 |

TABLE 2-continued

| 46 | Biotin-α-D-N-acetylneuraminide (2S,5R)-5-acetamido-4-hydroxy-3,3,4,5,6-pentamethyl-2-((5-((3aS,6aR)-2-oxohexahydro-1H-thieno[3,4-d]imidazol-4-yl)pentanoyloxy)methyl-6-(1,2,3-trihydroxypropyl)tetrahydro-2H-pyran-2-carboxylic acid | 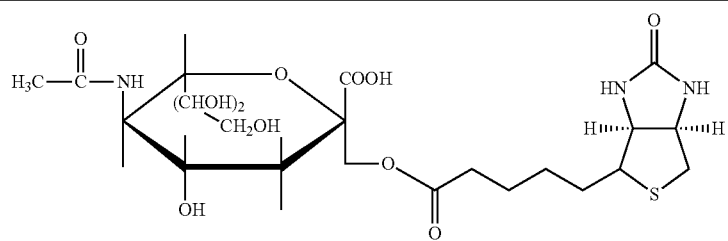 |
| 47 | Biotin-α-L-fucoside ((2R,5S)-3,4,5-trihydroxy-2,3,4,5,6,6-hexamethyl-tetrahydro-2H-pyran-2-yl)methyl 5-((3aS,6aR)-2-oxohexahydro-1H-thieno[3,4-d]imidazol-4-yl)pentanoate | 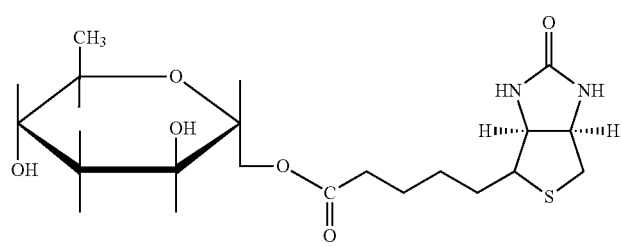 |
| 48 | Biotin lacto-N-bioside See end of table for name | 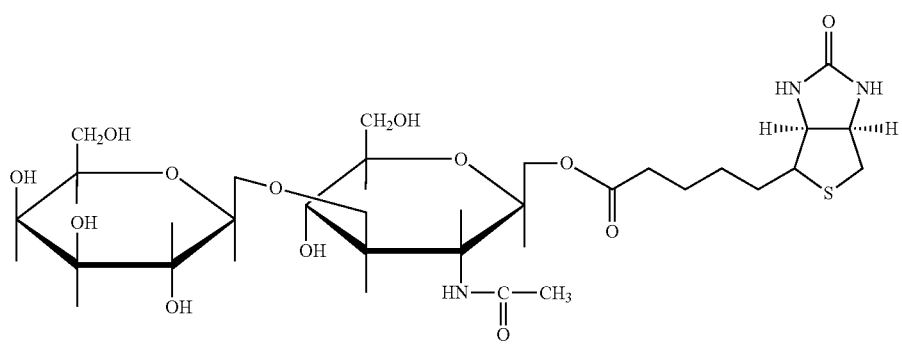 |
| 49 | Biotin-Lewis-A trisaccharide See end of table for name | 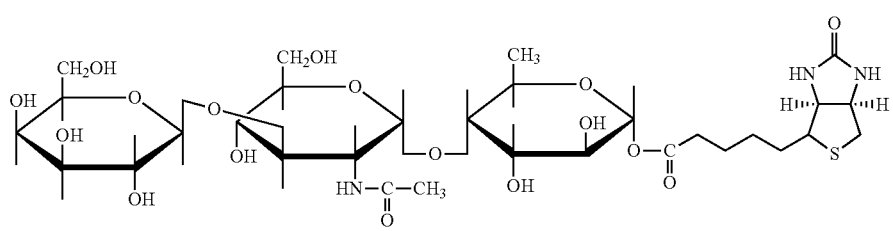 |

TABLE 2-continued

| 50 | Biotin-Lewis-Y tetrasaccharide See end of table for name | 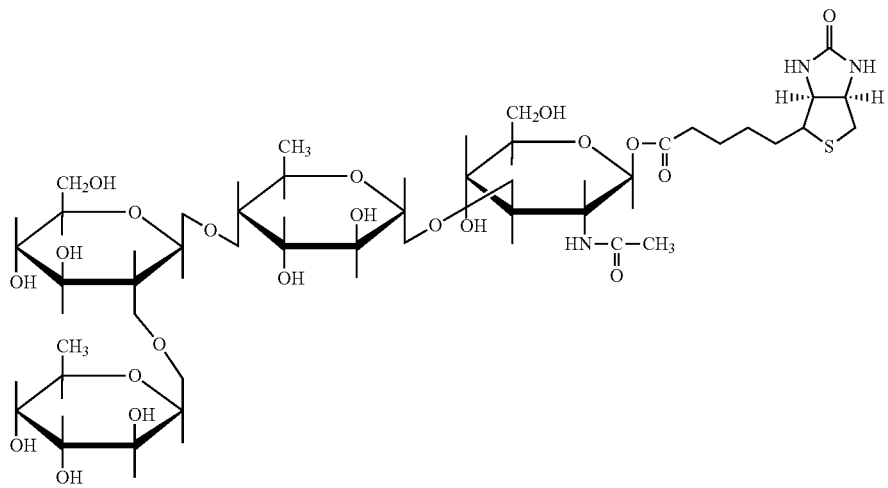 |
| --- | --- | --- |
| 51 | Biotin-α-D-mannopyranoside ((1R,4R)-2,3,4-trihydroxy-5-(hydroxymethyl)-1,2,3,4,5-pentamethyl-cyclohexyl)methyl 5-((3aS,6aR)-2-oxohexahydro-1H-thieno[3,4-d]imidazol-4-yl)pentanoate | 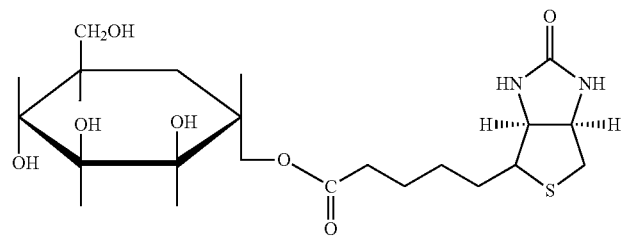 |
| 52 | biotin 6-O-phospho-α-D-mannopyranoside ((2R,5S)-3,4,5-trihydroxy-2,3,4,5,6-pentamethyl-6-(phosphonooxy-methyl)tetrahydro-2H-pyran-2-yl)methyl 5-((3aS,6aR)-2-oxohexahydro-1H-thieno[3,4-d]imidazol-4-yl)pentanoate | 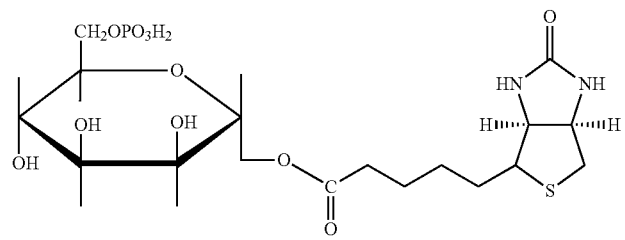 |

Names of Compounds 48-50:

48. ((2R,5S)-3-acetamido-5-hydroxy-6-(hydroxymethyl)-2,3,4,6-tetramethyl-4-(((((2S,5R)-3,4,5-trihydroxy-6-(hydroxymethyl)-2,3,4,5,6-pentamethyltetrahydro-2H-pyran-2-yl)methoxy)methyl)tetrahydro-2H-pyran-2-yl) methyl 5-((3aS,6aR)-2-oxohexahydro-1H-thieno[3,4-d] imidazol-4-yl)pentanoate ((2R,5S)-3-acetamido-5-hydroxy-6-(hydroxymethyl)-2,3,4,6-tetramethyl-4-(((((2S,5R)-3,4,5-trihydroxy-6-(hydroxymethyl)-2,3,4,5,6-pentamethyltetrahydro-2H-pyran-2-yl)methoxy) methyl)tetrahydro-2H-pyran-2-yl)methyl 5-((3aS,6aR)-2-oxohexahydro-1H-thieno[3,4-d]imidazol-4-yl)pentanoate
49. (2R,3R,5S)-5-(((((2S,3S,5S)-3-acetamido-5-hydroxy-6-(hydroxymethyl)-2,4,6-trimethyl-4-(((((2S,5R)-3,4,5-trihydroxy-6-(hydroxymethyl)-2,3,4,5,6-pentamethyltetra-hydro-2H-pyran-2-yl)methoxy)methyl)tetrahydro-2H-pyran-2-yl)methoxy)methyl)-3,4-dihydroxy-2,4,5,6,6-pentamethyltetrahydro-2H-pyran-2-yl5-((3aS,6aR)-2-oxohexahydro-1H-thieno[3,4-d]imidazol-4-yl)pentanoate
50. (2S,5S)-3-acetamido-4-(((((2R,5S)-5-(((((2R,5S)-4,5-di-hydroxy-6-(hydroxymethyl)-2,3,4,5,6-pentamethyl-3-(((((2S,5S)-3,4,5-trihydroxy-2,3,4,5,6,6-hexamethyltetra-hydro-2H-pyran-2-yl)methoxy)methyl)tetrahydro-2H-pyran-2-yl)methoxy)methyl)-3,4-dihydroxy-2,3,4,5,6,6-hexamethyltetrahydro-2H-pyran-2-yl)methoxy)methyl)-5-hydroxy-6-(hydroxymethyl)-2,3,4,5,6-pentamethyltetrahydro-2H-pyran-2-yl 5-((3aS,6aR)-2-oxohexahydro-1H-thieno[3,4-d]imidazol-4-yl)pentanoate Structures of iminobiotin compounds are not shown in Table 2. However, the iminobiotin structures are analogs of the biotin structure where the biotin group is replaced by an iminobiotin group. An example is shown below.

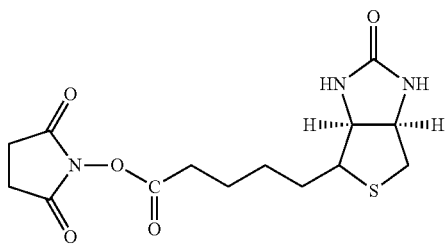

N-hydroxysuccinimide biotin

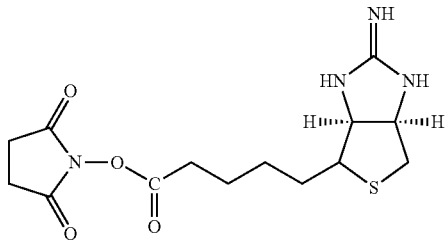

N-hydroxysuccinimide iminobiotin

In an embodiment of the invention, metal derived targeting agents may be polymeric or monomeric. Polymeric metal derive targeting agents are fully described in U.S. Pat. No. 7,169,410. Monomeric metal derived targeting agents are described in U.S. Pat. No. 4,603,044. Whether polymeric or monomeric, the compounds generally comprise a metal (typically purchased as an inorganic salt) that may be selected from the transition and inner transition metals or neighbors of the transition metals. The transition and inner transition metals from which the metal is selected include: Sc (scandium), Y (yttrium), La (lanthanum), Ac (actinium), the actinide series; Ti (titanium), Zr (zirconium), Hf (hafnium), V (vanadium), Nb (niobium), Ta (tantalum), Cr (chromium), Mo (molybdenum), W (tungsten), Mn (manganese), Tc (technetium), Re (rhenium), Fe (iron), Co (cobalt), Ni (nickel), Ru (ruthenium), Rh (rhodium), Pd (palladium), Os (osmium), Ir (iridium), and Pt (platinum). The neighbors of the transition metals from which the metal may be selected are: Cu (copper), Ag (silver), Au (gold), Zn (zinc), Cd (cadmium), Hg (mercury), Al (aluminum), Ga (gallium), In (indium), Tl (thallium), Ge (germanium), Sn (tin), Pb (lead), Sb (antimony) and Bi (bismuth), and Po (polonium). Preferably, the metal is chromium.

Non-limiting examples of useful salts include chromium chloride (III) hexahydrate; chromium (III) fluoride tetrahydrate; chromium (III) bromide hexahydrate; zirconium (IV) citrate ammonium complex; zirconium (IV) chloride; zirconium (IV) fluoride hydrate; zirconium (IV) iodide; molybdenum (III) bromide; molybdenum (III) chloride; molybdenum (IV) sulfide; iron (III) hydrate; iron (III) phosphate tetrahydrate, iron (III) sulfate pentahydrate, and the like.

In addition to a metal, the metal derived targeting agent comprises one or more complexing agents. A complexing agent is a compound capable of forming a water insoluble coordination complex with the preferred metal. There are several families of suitable complexing agents.

A complexing agent may be selected from the family of iminodiacetic acids of formula (1) wherein $R_1$ is loweralkyl, aryl, arylloweralkyl, or a heterocyclic substituent.

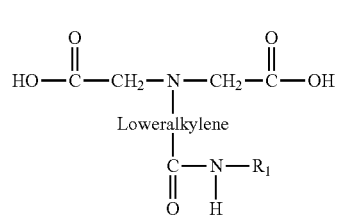

Suitable compounds of formula (1) include:
N-(2,6-diisopropylphenylcarbamoylmethyl) iminodiacetic acid;
N-(2,6-diethylphenylcarbamoylmethyl) iminodiacetic acid;
N-(2,6-dimethylphenylcarbamoylmethyl) iminodiacetic acid;
N-(4-isopropylphenylcarbamoylmethyl) iminodiacetic acid;
N-(4-butylphenylcarbamoylmethyl) iminodiacetic acid;
N-(2,3-dimethylphenylcarbamoylmethyl) iminodiacetic acid;
N-(2,4-dimethylphenylcarbamoylmethyl) iminodiacetic acid;
N-(2,5-dimethylphenylcarbamoylmethyl) iminodiacetic acid;
N-(3,4-dimethylphenylcarbamoylmethyl) iminodiacetic acid;
N-(3,5-dimethylphenylcarbamoylmethyl) iminodiacetic acid;
N-(3-butylphenylcarbamoylmethyl) iminodiacetic acid;
N-(2-butylphenylcarbamoylmethyl) iminodiacetic acid;
N-(4-tertiary butylphenylcarbamoylmethyl) iminodiacetic acid;
N-(3-butoxyphenylcarbamoylmethyl) iminodiacetic acid;
N-(2-hexyloxyphenylcarbamoylmethyl) iminodiacetic acid;
N-(4-hexyloxyphenylcarbamoylmethyl) iminodiacetic acid;
Aminopyrrol iminodiacetic acid;
N-(3-bromo-2,4,6-trimethylphenylcarbamoylmethyl) iminodiacetic acid;
Benzimidazole methyl iminodiacetic acid;
N-(3-cyano-4,5-dimethyl-2-pyrrylcarbamoylmethyl) iminodiacetic acid;
N-(3-cyano-4-methyl-5-benzyl-2-pyrrylcarbamoylmethyl) iminodiacetic acid; and
N-(3-cyano-4-methyl-2-pyrrylcarbamoylmethyl) iminodiacetic acid and other derivatives of N-(3-cyano-4-methyl-2-pyrrylcarbamoylmethyl) iminodiacetic acid of formula (2),

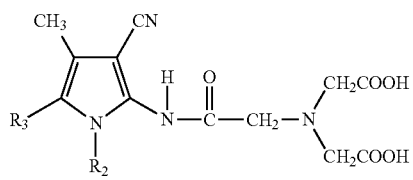

wherein $R_2$ and $R_3$ are the following:

| $R_2$ | $R_3$ |
|---|---|
| H | iso-$C_4H_9$ |
| H | $CH_2CH_2SCH_3$ |
| H | $CH_2C_6H_4$-p-OH |
| $CH_3$ | $CH_3$ |

| R$_2$ | R$_3$ |
|---|---|
| CH$_3$ | iso-C$_4$H$_9$ |
| CH$_3$ | CH$_2$CH$_2$SCH$_3$ |
| CH$_3$ | C$_6$H$_5$ |
| CH$_3$ | CH$_2$C$_6$H$_5$ |
| CH$_3$ | CH$_2$C$_6$H$_4$-p-OCH$_3$ |

Alternatively, the complexing agent may be selected from the family of imino diacid derivatives of formula (3), wherein R$_4$, R$_5$, and R$_6$ are independently selected at each occurrence and may be hydrogen, loweralkyl, aryl, arylloweralkyl, alkoxyloweralkyl, and heterocyclic.

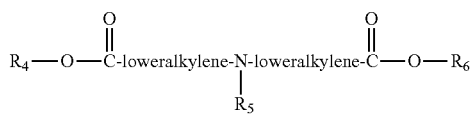

(3)

Suitable compounds of formula (3) include: N'-(2-acetylnaphthyl) iminodiacetic acid (NAIDA); N'-(2-naphthylmethyl) iminodiacetic acid (NMIDA); iminodicarboxymethyl-2-naphthylketone phthalein complexone; 3 (3:7a:12a:trihydroxy-24-norchol anyl-23-iminodiacetic acid; benzimidazole methyl iminodiacetic acid; and N-(5,pregnene-3-p-ol-2-oyl carbamoylmethyl) iminodiacetic acid.

The complexing agent may also be selected from the family of amino acids of formula (4),

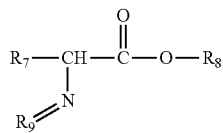

(4)

where R$_7$ is an amino acid side chain; wherein R$_8$ may be loweralkyl, aryl, and arylloweralkyl; and wherein R$_9$ is pyridoxylidene.

Suitable amino acids of the formula (4) are aliphatic amino acids, including, but not limited to: glycine, alanine, valine, leucine, isoleucine; hydroxyamino acids, including serine, and threonine; dicarboxylic amino acids and their amides, including aspartic acid, asparagine, glutamic acid, glutamine; amino acids having basic functions, including lysine, hydroxylysine, histidine, arginine; aromatic amino acids, including phenylalanine, tyrosine, tryptophan, thyroxine; and sulfur-containing amino acids, including cystine and methionine.

The complexing agent may also be selected from amino acid derivatives including, but not limited to (3-alanine-y-amino) butyric acid, O-diazoacetylserine (azaserine), homoserine, ornithine, citrulline, penicillamine and members of the pyridoxylidene class of compounds. Pyridoxylidene compounds include, but are not limited to: pyridoxylidene glutamate; pyridoxylidene isoleucine; pyridoxylidene phenylalanine; pyridoxylidene tryptophan; pyridoxylidene-5-methyl tryptophan; pyridoxylidene-5-hydroxytryptamine; and pyridoxylidene-5-butyltryptamine.

The complexing agent may likewise be selected from the family of diamines of formula (6):

(6)

wherein R$_{10}$ is hydrogen, loweralkyl, or aryl; R$_{11}$ is loweralkylene or arylloweralky; R$_{12}$ and R$_{13}$ are independently selected at each occurrence and may be hydrogen, loweralkyl, alkyl, aryl, arylloweralkyl, acylheterocyclic, toluene, sulfonyl or tosylate.

Examples of suitable diamines of formula (6) include, but are not limited to, ethylenediamine-N,N diacetic acid; ethylenediamine-N,N-bis(-2-hydroxy-5-bromophenyl) acetate; N'-acetylethylenediamine-N,N diacetic acid; N'-benzoyl ethylenediamine-N,N diacetic acid; N'-(p-toluenesulfonyl) ethylenediamine-N,N diacetic acid; N-(p-t-butylbenzoyl) ethylenediamine-N,N diacetic acid; N'-(benzenesulfonyl) ethylenediamine-N,N diacetic acid; N'-(p-chlorobenzenesulfonyl)ethylenediamine-N,N diacetic acid; N'-(p-ethylbenzenesulfonyl ethylenediamine-N,N diacetic acid; N'-acyl and N'-sulfonyl ethylenediamine-N,N diacetic acid; N'-(p-n-propylbenzenesulfonyl)ethylenediamine-N,N diacetic acid; N'-(naphthalene-2-sulfonyl)ethylenediamine-N,N diacetic acid; and N'-(2,5-dimethylbenzenesulfonyl) ethylenediamine-N,N diacetic acid.

Other, non-limiting examples of complexing compounds or agents include penicillamine; p-mercaptoisobutyric acid; dihydrothioctic acid; 6-mercaptopurine; kethoxal-bis(thiosemicarbazone); Hepatobiliary Amine Complexes, 1-hydrazinophthalazine (hydralazine); sulfonyl urea; Hepatobiliary Amino Acid Schiff Base Complexes; pyridoxylidene glutamate; pyridoxylidene isoleucine; pyridoxylidene phenylalanine; pyridoxylidene tryptophan; pyridoxylidene 5-methyl tryptophan; pyridoxylidene-5-hydroxytryptamine; pyridoxylidene-5-butyltryptamine; tetracycline; 7-carboxy-p-hydroxyquinoline; phenolphthalein; eosin I bluish; eosin I yellowish; verograffin; 3-hydroxyl-4-formyl-pyridene glutamic acid; Azo substituted iminodiacetic acid; hepatobiliary dye complexes, such as rose bengal; congo red; bromosulfophthalein; bromophenol blue; toluidine blue; and indocyanine green; hepatobiliary contrast agents, such as iodipamide; and ioglycamic acid; bile salts, such as bilirubin; cholgycyliodohistamine; and thyroxine; hepatobiliary thio complexes, such as penicillamine; p-mercaptoisobutyric acid; dihydrothiocytic acid; 6-mercaptopurine; and kethoxal-bis (thiosemicarbazone); hepatobiliary amine complexes, such as 1-hydrazinophthalazine (hydralazine); and sulfonyl urea; hepatobiliary amino acid Schiff Base complexes, including pyridoxylidene-5-hydroxytryptamine; and pyridoxylidene-5-butyltryptamine; hepatobiliary protein complexes, such as protamine; ferritin; and asialo-orosomucoid; and asialo complexes, such as lactosaminated albumin; immunoglobulins, G, IgG; and hemoglobin.

Compositions not Including a Therapeutic Agent

Compositions of the invention may further include one or more associated therapeutic agents, however a therapeutic agent need not be present. In embodiments of the invention that do not have a therapeutic agent, i.e., compositions that are substantially free of a therapeutic agent, the composition comprises constituents prepared from the lipids previously disclosed herein, a biotin-derived targeting agent, and gelatin. The constituents can comprise a dynamically sized liposome, liposome fragment, and lipid particle, wherein the lipid particle comprises at least one lipid component and the liposome or liposome fragment can comprise at least two lipid components.

It has been surprisingly found that administration of the above described compound has the ability to affect efficient delivery of a biotin and/or a biotin-derived compound, overcoming the solubility issues plaguing the oral delivery of free biotin and biotin derived compounds. Moreover, the composition of the invention has surprisingly shown that it can affect weight loss in a patient suffering from Type 2 diabetes at an effective dosage of biotin at least 5 to 10 times lower than previously reported. It has further been surprisingly discovered that administration of the above described compound results in drop in fasting blood glucose in a patient and reduces HbA1c in Type 2 diabetics (HbA1c, also known as glycated hemoglobin, is a form of hemoglobin used primarily to identify the average plasma glucose concentration in a patient over a prolonged period of time).

The above described compound can be administered at any time during the day or night. It can be administered as a single dose, or as multiple doses per 24 hour period, such as 2, 3, 4, 5, 6, 7, 8, 9 or more doses depending upon the needs of the patient. In certain embodiments, the composition can be administered in 1, 2, 3, or 4 doses.

Dosing can be accomplished before, during, or after a meal. Alternatively, dosing can be accomplished before bed time or shortly after waking. In one embodiment, the composition described above can be administered before breakfast, before lunch, before dinner, and shortly before bedtime.

The above described composition can contain an effective amount of biotin of from about 1 µg to about 10,000 µg, including all whole and partial increments there between. In other embodiments, a composition of the invention can contain from about 10 µg to about 5,000 µg of an effective amount of biotin, including all whole and partial increments there between, as well as all ranges included therein. The effective amount of biotin in this embodiment of the invention is based on the total quantity of biotin-derived targeting agent in the composition. For example, a composition comprising 10 mg biotin DHPE would contain an effective amount of biotin of about 2.6 mg. A composition comprising 5 mg of D-biotin as the biotin-derived targeting agent would contain an effective dose of 5 mg of biotin.

In one embodiment, the composition can contain an effective amount of about 78 µg biotin. In other embodiments, the composition can contain an effective amount of about 78 µg biotin divided by the total number of doses given per day. Thus, and by way of example only, a composition given four times a day could contain an effective amount of 19.5 µg biotin in each dose. (19.5 µg=78 µg biotin/4 dose day).

In another embodiment, the composition can contain an effective amount of about 100 µg biotin. In other embodiments, the composition can contain an effective amount of about 100 µg biotin divided by the total number of doses given per day. Thus, and by way of example only, a composition given four times a day could contain an effective amount of 25 µg biotin in each dose. (25 µg=100 µg biotin/4 dose day).

In other embodiments, the composition can contain an effective amount of about 234 µg biotin, or an effective amount of about 234 µg biotin divided by the total number of doses given per day. In other embodiments, the therapeutic agent free composition can contain an effective amount of about 5 mg biotin. In still other embodiments, the above described composition can contain an effective amount of about 5 mg biotin divided by the total number of doses given per day.

In a preferred embodiment, a composition can be formed from lipid components and a biotin-derived targeting agent mixed in accordance with the following: approximately 61 mole percent 1,2 distearoyl-sn-glycero-3-phosphocholine, approximately 22 mole percent dihexadecyl phosphate, approximately 16 mole percent cholesterol, and about 1 mole percent of a biotin-derived targeting agent. In certain embodiments the biotin-derived targeting agent is biotin DHPE, biotin-X-DHPE, or D-biotin. The composition can then be mixed with an amount of gelatin.

In another preferred embodiment, a composition can be formed from lipid components and a biotin-derived targeting agent mixed in accordance with the following: about 56 mole percent 1,2 distearoyl-sn-glycero-3-phosphocholine, about 21 mole percent dihexadecyl phosphate, about 15 mole percent cholesterol, and about 8 mole percent of a biotin-derived targeting agent. In certain embodiments the biotin-derived targeting agent is biotin DHPE, biotin-X-DHPE, or D-biotin. An embodiment wherein the biotin-derived targeting agent is biotin DHPE is shown in the table below.

|        | 1,2 distearoyl-sn-glycero-3-phosphocholine | dihexadecyl phosphate | Cholesterol | Biotin DHPE |
|--------|--------------------------------------------|-----------------------|-------------|-------------|
| MW     | 790                                        | 547                   | 387         | 940         |
| g      | 6.04                                       | 1.54                  | 0.799       | 1.047       |
| mg/mL  | 36.3                                       | 9.24                  | 4.8         | 6.3         |
| wt. %  | 64.09                                      | 16.31                 | 8.47        | 11.12       |
| mol %  | 56.06                                      | 20.64                 | 15.14       | 8.17        |

Any of the above described compositions can then be mixed with an amount of gelatin, including from about 200 to about 1,000 mg as well as any whole or partial increments there between. In particular embodiments, the amount of gelatin is about 230 mg.

In other embodiments, a liquid suspension of the composition can be used without further modification and without being added to gelatin.

While it is preferred that the biotin-derived targeting agent is delivered as a component of the composition of the invention, in certain embodiments, the biotin-derived targeting agent can be administered to a patient in need thereof free of any additional lipid components. In certain embodiments, the biotin-derived targeting agent that is administered is biotin DHPE, or a salt thereof. In other embodiments, the biotin targeting agent is biotin-X-DHPE, or a salt thereof.

The above described composition of the invention (or free biotin-derived targeting agent) can also be co-administered with one or more additional therapeutic agents useful for inducing weight loss. Examples of therapeutic agents useful for inducing weight loss include, but are not limited to, orlistat, sibutramine, phendimetrazine tartrate, methamphetamine, IONAMIN™, phentermine, fenfluramine, dexfenfluramine, chitosan, chromium picolinate, conjugated linoleic acid, green tea extract, guar gum, hoodia, a combination of topiramate and phentermine, a combination of bupropion and zonisamide, a combination of bupropion and naltrexone, a combination of phentermine and fluoxetine, a combination of phentermine and sertraline, a combination of phentermine and citalopram, a combination of phentermine and escitalopram, and a combination of phentermine and trazodone.

It is also contemplated that any of the particular embodiments described above can be administered to affect weight maintenance. Moreover, any of the embodiments described above can be provided as a food additive, dietary supplement, or as beverage additive. The composition can be added in any amount to food, taken in any amount as a dietary supplement, or added to a beverage as appropriate. In certain embodiments, the amount of composition added to a food/beverage or taken as a dietary supplement will not exceed an effective amount of biotin of about 10,000 µg/day. In other embodiments, the amount of composition added to a food or beverage or taken as a dietary supplement will contain an effective amount of between about 10 and about 10,000 µg biotin/day, including all whole and partial increments there between, as well as all possible sub-ranges.

Compositions of the Invention Including One or More Therapeutic Agents

The constituents of the composition of the present invention may associate with one or more therapeutic agents and/or diagnostic agents. Without wishing to be bound by any particular theory, it is believed that constituents having diameters of 20 nanometers or less are sufficiently small to pass through intercellular gaps, thus enabling transport of the associated therapeutic agent or diagnostic agent from the lumen of the gut into the portal blood.

The associated therapeutic agents and/or diagnostic agents may be bound covalently or noncovalently to one or more constituents of the composition of the present invention. In embodiments of the invention wherein the associated therapeutic or diagnostic agents are bound covalently, the associated therapeutic agent or diagnostic agent may be bound to a chemical group that can be functionalized. Examples of functionalizable groups include, but are not limited to, hydroxy, amino, carboxy, and amido groups.

Examples of therapeutic agents that may be covalently bound to a constituent of a composition of the present invention include poly-peptides and/or proteins, such as, but not limited to, D-biotin, GLP-1, insulin, calcitonin, interferon, uricase, tissue plasminogen activator, thymoglobin, various vaccines, heparin, heparin analogs, antithrombin III, filgrastin, pramilitide acetate, exanatide, epifibatide, and antivenins, blood clotting factors including, but not limited to, Factors VII and VIII, various small molecules, such as, for example, D or L thyroxine or serotonin, nucleic acids, DNA or RNA sequences, immunoglobulins, such as, but not limited to, IgG and IgM, and a variety of monoclonal antibodies, such as but not limited to, rituximab, trastuzumab, and glycolipids that act as therapeutic agents, and in addition, other larger proteins, such as, for example, human growth hormone ("HGH"), erythropoietin, and parathyroid hormone. In preferred embodiments, the covalently attached therapeutic is D-biotin.

Examples of diagnostic agents that may be covalently bound to a constituent of a composition of the present invention include diagnostic contrast agents such as, but not limited to, gold and a gadolinium. Other diagnostic agents include radioactive materials such as radioactive isotopes of common atoms including, but not limited to, $^{13}C$, $^{68}Ge$, $^{18}F$, and $^{125}I$. These contrast and radioactive agents may be covalently attached to a constituent of the composition directly through covalent attachment to a lipid component or targeting agent. Alternatively, and where chemically appropriate, the diagnostic agent may be bound to a ligand such as DADO (2'-deoxyadenosine), which is itself covalently attached to a lipid component or targeting agent.

Alternatively, and where appropriate chemically, a constituent of a composition of the invention, may associate with the aforementioned diagnostic or therapeutic agents via non-covalent interactions. Non-covalent interactions enable compatibility of a constituent of the composition of the present invention with a wide variety of diagnostic and therapeutic agents.

Examples of therapeutic agents that can associate with a composition of the invention non-covalently include, but are not limited to, D-biotin, insulin, interferon, rituximab, trastuzumab, uricase, tissue plasminogen activator, thymoglobin, various vaccines, heparin, heparin analogs, anithrombin III, filgrastin, pramilitide acetate, exanatide, epifibatide, antivenins, IgG, IgM, blood clotting Factors VII and VIII, HGH, GLP-1, erythropoietin, parathyroid hormone, serotonin, D- or L-thyroxine, calcitonin, monoclonal antibodies, as well as other therapeutic peptides. In preferred embodiments, the non-covalently associated therapeutic agent is D-biotin. D-biotin acts at the liver to induce weight loss.

Association of D-biotin can be achieved via addition of a low molarity solution of D-biotin to an aqueous suspension of constituents. In this embodiment, the number of lipid molecules involved in the assembly of the constituents far surpasses the number of molecules of D-biotin interlaced and/or combined either on or within the constituents' matrices. This high ratio of constituents to D-biotin is believed to minimize the molecular interactions between D-biotin and the constituents, insuring that the self-assembly and self-organization process of the constituents of the composition of the present invention are not disrupted. This high ratio is believed to facilitate the formation of a stable constituent/D-biotin association.

Without wishing to be bound by a particular theory, it is believed that the quantity of therapeutic agent(s) associated with a constituent of a composition of the present invention appears to be a function of loading time and lipid concentration. As the lipid component concentration in aqueous media is increased, additional therapeutic agents associate with a constituent of a composition of the present invention. The time required for loading the therapeutic agent may be anywhere from several hours to about one week.

Dosing of a composition comprising D-biotin as the associated therapeutic agent can be accomplished before, during, or after a meal. Alternatively, dosing can be accomplished before bed time or shortly after waking. In one embodiment, the composition described above can be administered before breakfast, before lunch, before dinner, and shortly before bedtime.

The amount of associated D-biotin can be from about 1 to about 10,000 µg of biotin, including all whole and partial increments there between. In other embodiments, the amount of associated D-biotin can be about 10 µg to about 5,000 µg, including all whole and partial increments there between, as well as all ranges included therein.

In one embodiment, the composition can contain about 78 µg D-biotin. In other embodiments, the composition can contain 78 µg D-biotin divided by the total number of doses given per day. Thus, and by way of example only, a composition given four times a day could contain 19.5 µg D-biotin in each dose. (19.5 µg=78 µg D-biotin/4 dose day).

In other embodiments, the composition can contain about 234 µg D-biotin, or about 234 µg D-biotin divided by the total number of doses given per day. In other embodiments, the therapeutic agent free composition can contain 5 mg D-biotin. In still other embodiments, the therapeutic agent free composition can contain 5 mg D-biotin divided by the total number of doses given per day.

In a preferred embodiment, a composition with D-biotin as the associated therapeutic agent can be formed from lipid components and, optionally, a biotin-derived targeting agent mixed in accordance with the following: approximately 61 mole percent 1,2 distearoyl-sn-glycero-3-phosphocholine, approximately 22 mole percent dihexadecyl phosphate, approximately 16 mole percent cholesterol, and about 1 mole percent of a biotin-derived targeting agent (if present). In certain embodiments the biotin-derived targeting agent is biotin DHPE, biotin-X-DHPE, or D-biotin.

A composition having D-biotin as the associated therapeutic agent can also be co-administered with one or more additional therapeutic agents useful for inducing weight loss. Examples of therapeutic agents useful for inducing weight loss include, but are not limited to, orlistat, sibutramine, phendimetrazine tartrate, methamphetamine, IONAMIN™, phentermine, fenfluramine, dexfenfluramine, chitosan, chromium picolinate, conjugated linoleic acid, green tea extract, guar gum, hoodia, a combination of topiramate and phentermine, a combination of bupropion and zonisamide, a combination of bupropion and naltrexone, a combination of phentermine and fluoxetine, a combination of phentermine and sertraline, a combination of phentermine and citalopram, a combination of phentermine and escitalopram, and a combination of phentermine and trazodone.

It is also contemplated that a composition of the invention having D-biotin as the associated therapeutic agent can be administered to affect weight maintenance, or provided as a food additive, dietary supplement, or as beverage additive. The composition can be added in any amount to food, taken in any amount as a dietary supplement, or added to a beverage as appropriate. In certain embodiments, the amount of composition added to a food/beverage or taken as a dietary supplement will not exceed an effective dose of D-biotin of about 10,000 µg/day. In other embodiments, the amount of composition added to a food or beverage or taken as a dietary supplement will include between about 10 and about 10,000 µg D-biotin/day, including all whole and partial increments there between, as well as all possible sub-ranges.

The low concentration of therapeutic agent relative to the concentration of the constituents of the composition of the present invention is unique among lipid particle delivery systems. Typically, liposome or liposome-like delivery systems have employed a much larger quantity of therapeutic agent. The efficacy this embodiment of the present combination shows that it is possible to utilize less therapeutic agent while still obtaining a pharmacologically desirable result in the patient. This embodiment of the invention therefore provides an advantageous therapeutic option.

In other embodiments the addition of a higher concentration of therapeutic agent may be both desirable and advantageous. The constituent members of a composition of the present invention are capable of associating with, and tolerating, higher molarity solutions of any given therapeutic agent.

Insulin can also be therapeutic agent associated with a composition of the invention. FIG. 1 illustrates a constituent/HTM/insulin construct. Insulin molecules bind to the surface of the constituent via non-covalent electrostatic interactions.

Serotonin, like insulin and D-biotin, may also be delivered to the liver utilizing a constituent/HTM complex according to the invention. Serotonin acts jointly with insulin at the level of the liver to activate hepatic glucose storage during a portal (oral) glucose load. In order to achieve the desired effect, serotonin must be delivered to the liver. Non-targeted serotonin, introduced via injection or oral delivery in pharmacologically acceptable doses cannot effectively induce the desired activity. Therefore, an embodiment of the invention comprising a constituent/HTM/serotonin construct provides a highly desirable delivery mechanism for this important gluco-regulatory hormone. In an embodiment of the invention designed for the delivery of serotonin, the lipid components selected to form the constituents of the composition include approximately 62 mole percent, 1,2-distearoyl-sn-glycero-3-phosphocholine, approximately 22 mole percent dihexadecyl phosphate, approximately 16 mole percent cholesterol and about 1 mole percent of a targeting agent.

Calcitonin is a hormone that regulates bone metabolism. Due to the high prevalence of diseases such as osteoporosis, an oral formulation of this hormone is highly desirable. Presently calcitonin is only deliverable via injection. In an embodiment of the invention designed for the delivery of calcitonin, the lipid components selected to form the constituents of the composition including calcitonin include approximately 62 mole percent, 1,2-distearoyl-sn-glycero-3-phosphocholine, approximately 22 mole percent dihexadecyl phosphate, and approximately 16 mole percent cholesterol.

GLP-1 is a peptide that acts at both the liver and pancreas. In the liver, GLP-1 acts to stimulate glycogen accumulation during a meal. However, prior art administration methods where GLP-1 is administered orally evidence poor bioavailability and reduced efficacy upon oral dosing. In an embodiment of the present invention, GLP-1 associates with a constituent of a composition of the invention form a constituent/GLP-1 construct. The constituent/GLP-1 construct may further include a targeting agent. Preferably, the lipid components selected to form the constituents of the composition including GLP-1 include approximately 62 mole percent 1,2-distearoyl-sn-glycero-3-phosphocholine, approximately 22 mole percent dihexadecyl phosphate, and approximately 16 mole percent cholesterol.

Thyroxine, like insulin, is also not generally orally bioavailable. In an embodiment of the invention, though, thyroxine may associate with a constituent of a composition of the invention forming a constituent/thyroxine construct. Preferably, the lipid components selected to form the constituents of the composition including thyroxine include approximately 62 mole percent, 1,2-distearoyl-sn-glycero-3-phosphocholine, approximately 22 mole percent dihexadecyl phosphate, approximately 16 mole percent cholesterol, and approximately 1 mole percent Biotin DHPE.

Although the invention has been described in terms of specific therapeutic agent/constituent constructs, any of the therapeutic agents described herein may associate with a constituent of the invention to form a therapeutic agent/constituent construct.

Covalently Attached Therapeutic Agents

In certain embodiments of the invention, the therapeutic agent may be covalently attached to a lipid component of the invention. Typically, however, the covalent attachment of the therapeutic agent to the lipid component is not direct, but is mediated by a linker of the form $-C(O)(CH_2)_nSR$, wherein an amide, ester, or thioamide bond is formed between the therapeutic agent and the linker. Preferably, n is an integer between 1 and 10. Even more preferably, n is 1, 2, or 3. When the linker is being attached to the therapeutic agent, R is typically a protecting group such as $-C(O)CH_3$. Other appropriate thiol protecting groups may be found in Green's Protective Groups in Organic Synthesis, Wuts, et al, 4$^{th}$ edition, 2007.

After the linker is bound to the therapeutic agent, the protecting group, R, is removed from the linker to reveal a free thiol group. Preferably, the protecting group is removed under conditions that do not perturb the now attached therapeutic agent. This thiol may then undergo a Michael reaction with a lipid component such as MPB-PE to form a thio ether. Preferably, lipid component MPB-PE is already incorporated into a constituent of a compound of the invention, however, the linker may be bound to the MPB-PE prior to its incorporation a constituent of the invention. The order of reactions will depend upon the therapeutic agent's ability to tolerate certain reaction conditions. In the case of complex proteins which may denature at high temperatures, it is preferable to perform the Michael reaction after MPB-PE has been incorporated into a constituent of the compound of the invention.

In an example of a covalent interaction, IgG was covalently linked to a lipid component of a constituent of the invention to form a constituent/IgG construct. IgG is an antibody that is not normally orally bioavailable. In this embodiment of the invention, the lipid components selected to form the constituents of the constituent/IgG construct include approximately 68 mole percent 1,2-dipalmitoyl-sn-glycero-3-phosphocholine, approximately 18 mole percent dihexadecyl phosphate, approximately 9 mole percent cholesterol, and approximately 3 mol percent MPB-PE.

In order to form the constituents of the invention, 1,2-dipalmitoyl-sn-glycero-3-phosphocholine, dihexadecyl phosphate, and cholesterol were microfluidized as set forth earlier herein to form constituents with an upper size limit of between 50 and 60 nanometers. This suspension of constituents was then transferred to a round bottom flask that had been coated with a thin film of MPB-PE. The suspension was heated to about 62° C., with the temperature not falling below 60° C. or exceeding 65° C. The heated suspension was subsequently stirred for 15 minutes until all of the MPB-PE had been incorporated into the constituents of the invention.

Separately, IgG was reacted with a 10 fold excess of linker precursor I (R=CH$_3$C(O), n=1), below, to form II. Compound II was then purified using a 2.5×25 cm Sephadex G-25 column equilibrated with 18 mM phosphate buffer plus 1.0 mM EDTA buffer at pH 7.4.

Next, the acetyl protecting group on compound II was removed by stirring compound II with 50 mM hydroxylamine hydrochloride in 18 mM sodium phosphate buffer containing 1.0 mM EDTA (pH 7.4) for 2 hours at ambient temperature. The resulting free thiol, III, was purified on 2.5×25 cm Sephadex G-25 column, as set forth for compound II.

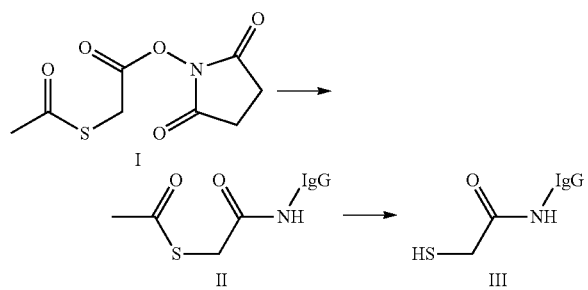

Immediately following purification, 200 μ-moles of compound III was mixed with 10 ml of the constituent solution prepared earlier. The reaction mixture was stirred for 15 minutes, during which time compound III underwent a Michael reaction with the maleimide functionality of the MBP-PE incorporated into the constituents of the invention. The conjugation reaction was stopped, and excess III removed, by the addition of a 50× molar excess of N-ethylmaleimide.

Although the above example was described with respect to IgG, it is equally applicable to any therapeutic agent with a basic nitrogen or free hydroxyl group, or other functionalizable group, able to bind to the linker or linker precursor.

Stability

Although constituent members of a composition of the present invention are formulated in aqueous media, the constituent members of the composition do not exhibit long term stability in water. Specifically, water aids hydrolysis of any acyl chains present in any of the lipid components of the compositional constituents. The aqueous environment also allows for the ready oxidation of any unsaturated acyl chains present in any of the lipid components. In a preferred embodiment of the present invention, the constituents of the composition of the present invention may be protected for long term storage via interaction with a proteoglycan such as a modified collagen, known generically as dry granulated gelatin. Dry granulated gelatin, when contacted with an aqueous suspension of constituents, reacts with water, stabilizes the constituents, and forms a composition of the present invention.

The reaction of dried granulated gelatin with an aqueous suspension of constituents of a composition of the present invention results in a semi-solid colloidal gel that shields the constituents from direct interaction with water. Any water not associated with gelatin is slowly evaporated via refrigerated storage at about 2° to about 8° C. The water may, however, be removed via techniques including, but not limited, freeze drying and spray drying.

This results in a pellet like "dry" constituent/gelatin complex which is the composition of the invention. In the composition, the constituent elements are partially dehydrated in a reversible manner and sequestered by the proteinaceous lattice of dry gelatin. This sequestration is enabled by structured water, structured lipid and structured gelatin all interacting through hydrogen bonding, ionic bonding, van der Waal's interactions, and hydrophobic bonding between the lipid components, water, and protein structures, i.e., insulin. This evidences that gelatin is not acting as an emulsifying or suspending agent. As a result, the "dry" pellet is stable for long term storage because the activity of water has been mitigated. These pellets can be further processed to a granulated or free-flowing powder for final capsule filling or tabletting, while maintaining their stability.

Upon oral administration to a patient, the "dry" pellet becomes hydrated and once again assumes a semi-solid colloidal gel state. Upon further exposure to the gastric environment, the gel becomes liquid as gelatin is solubilized. Once the gelatin is completely solubilized, the constituent members of the composition of the invention rehydrate, resulting in the formation of a new suspension of constituents within the gastric environment. The reconstituted constituents may then be absorbed into the portal blood flow.

It is important to realize that the role of gelatin in this aspect of the invention is as an active stabilizer of the composition and not an inert filler as is commonly found in oral formulations of many other pharmaceutical compositions. That said, the additional use of gelatin as an inert filler in addition to the aforementioned use is also contemplated.

Although gelatin is used in a preferred embodiment of the invention, other gelatin like compounds may be used as well. Examples of agents that will act as active stabilizers include, but are not limited to, acacia (gum arabic), agar (agar-agar; vegetable gelatin; gelosa; Chinese or Japanese gelatin), alginic acid, sodium alginate (alginic acid; sodium salt; algin; Manucol; Norgine; Kelgin), carbomer (carboxypolymethylene), carrageenan, carboxymethylcellulose sodium (carbose D; carboxymethocel S; CMC; cellulose gum), powdered cellulose (Degussa), hydroxyethyl cellulose (cellulose; 2-hydroxyethyl ether; Cellosize; Natrosol), hydroxypropyl cellulose (cellulose; 2-hydroxypropyl ether; Klucel), hydroxypropyl methylcellulose (cellulose; 2-hydroxypropyl methyl ether), methycellulose (cellulose; methyl ether Methocel), povidone (2-pyrrolidinone; 1-ethenyl-; homopolymer; polyvinylpyrrolidone), tragacanth (gum tragacanth; Hog Gum; Goat's Thorn), and xanthan gum (Keltrol). Like gelatin, and where appropriate, these compounds may also be used as inert fillers.

Formulations

A formulation of a composition of the invention—hereinafter "composition"—for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, aqueous suspensions, or emulsions.

A tablet comprising the composition of the present invention, for example, be made by compressing or molding the composition optionally with one or more additional ingredients. Compressed tablets may be prepared by compressing, in a suitable device, the composition in a free-flowing form such as a powder or granular preparation, optionally mixed with one or more of a binder, a lubricant, an excipient, a surface active agent, and a dispersing agent. Molded tablets may be made by molding, in a suitable device, the composition, a pharmaceutically acceptable carrier, and at least sufficient liquid to moisten the mixture.

Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the composition. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the composition may be made using a physiologically degradable composition, such as gelatin. Such hard capsules comprise the active ingredient, and may further comprise additional ingredients including, for example, an inert solid diluent such as calcium carbonate, calcium phosphate, kaolin or cellulose acetate hydrogen phthalate.

Soft gelatin capsules comprising the composition may be made using a physiologically degradable composition, such as gelatin.

Liquid formulations of the composition which are suitable for oral administration may be prepared, packaged, and sold either in liquid form or in the form of a dry product intended for reconstitution with water or another suitable vehicle prior to use, subject to the stability limitations disclosed earlier.

Liquid suspensions may be prepared using conventional methods to achieve suspension of the constituents in an aqueous vehicle. Aqueous vehicles include, for example, water and isotonic saline. Oily vehicles may only be used to the extent that such solvents are not incompatible with the constituents of the composition of the present invention. To the extent that an oily suspension is not incompatible with the constituents of the composition of the present invention, an oily suspension may further comprise a thickening agent.

Liquid suspensions may further comprise one or more additional ingredients to the extent that said ingredients do not disrupt the structures of the constituents of the composition of the invention. Examples of additional ingredients include, but are not limited to, suspending agents, dispersing or wetting agents, emulsifying agents, demulcents, preservatives, buffers, salts, flavorings, coloring agents, and sweetening agents.

Known suspending agents include, but are not limited to, sorbitol syrup, sodium alginate, polyvinylpyrrolidone, gum tragacanth, gum acacia, and cellulose derivatives such as sodium carboxymethylcellulose, methylcellulose, hydroxypropylmethylcellulose.

Known emulsifying agents include, but are not limited to acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin.

Powdered and granular formulations of a pharmaceutical preparation of the invention may be prepared using known methods. Such formulations may be administered directly to a subject, used, for example, to form tablets, to fill capsules, or to prepare an aqueous suspension or solution by addition of an aqueous vehicle thereto. Each of these formulations may further comprise one or more of dispersing or wetting agent, a suspending agent, and a preservative. Additional excipients, such as fillers and sweetening, flavoring, or coloring agents, may also be included in these formulations.

Methods of Treating Diseases

Diseases, such as diabetes may be treated by orally administering a compound of the invention wherein insulin is the associated therapeutic agent. Similarly, diabetes may be treated by orally administering a compound of the invention wherein insulin is the associated therapeutic and wherein another form of insulin is co-administered. Routes of co-administration include, but are not limited to, oral administration, intramuscular injection, inhalation, intravenous injection, intra-arterial injection, as well as any other form of administration.

Although a physician will be able to select the appropriate dose for a given patient, the range of doses that may be delivered in a given formulation of a compound of the invention is from about 1 to about 40 units, but may be 5, 10, 15, 20, 25, 30, or 35 units. A given formulation may, however, contain any whole or partial integer therebetween and may exceed 40 units.

Kits

The invention also includes a kit comprising a composition of the invention and an instructional material which describes administering the composition to a mammal. In another embodiment, this kit comprises a composition of the invention, insulin for co-administration, as well as instructional material which describes the co-administration process.

As used herein, an "instructional material" includes a publication, a recording, a diagram, or any other medium of expression which can be used to communicate the usefulness of the composition of the invention in the kit for effecting alleviation of the various diseases or disorders recited herein.

Optionally, or alternatively, the instructional material may describe one or more methods of alleviating the diseases or disorders in a cell or a tissue of a mammal. The instructional material of the kit may, for example, be affixed to a container which contains the invention or be shipped together with a container which contains the invention. Alternatively, the instructional material may be shipped separately from the container with the intention that the instructional material and the compound be used cooperatively by the recipient.

EXPERIMENTAL EXAMPLES

The invention is now described with reference to the following examples. These examples are provided for the purpose of illustration only and the invention should in no way be construed as being limited to these examples but rather should be construed to encompass any and all variations which become evident as a result of the teaching provided herein.

Experiment 1—Administration of Compositions not Containing a Targeting Agent

A composition whose constituent members were created from a mixture of lipid components comprising approximately 62 mole percent 1,2-distearoyl-sn-glycero-3-phosphocholine, approximately 22 mole percent dihexadecyl phosphate, approximately 16 mole percent cholesterol, and no targeting agent was prepared according to the microfluidization procedure generally described herein. A known portion of the lipid component comprised $^{14}C$ labeled phospholipid. Following filtration through a 0.2 micron filter, the average constituent size was less than 100 nm as measured with a Coulter Sub-micron Particle Size Analyzer.

Figure 2:
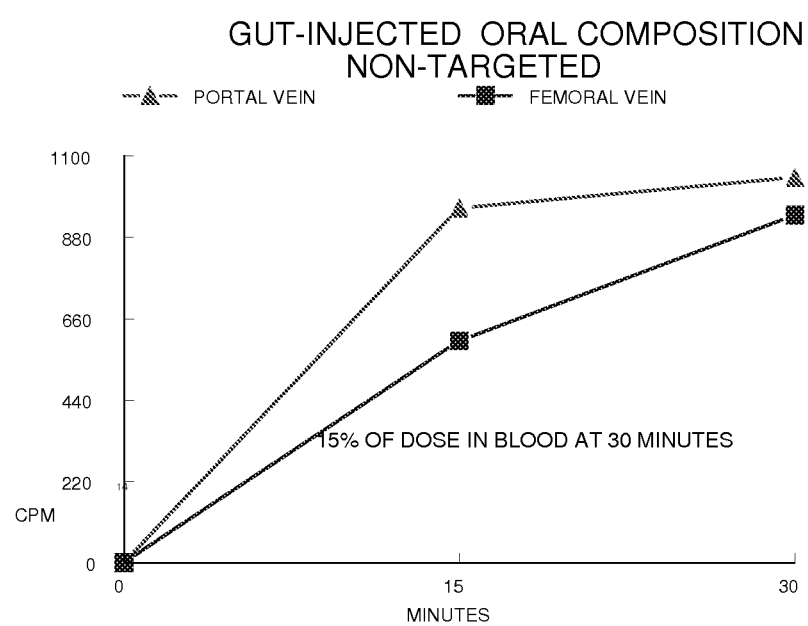
FIG. 2 is a graph depicting the counts of $^{14}$C radio-labeled phospholipid found in the femoral and portal veins 15 and 30 minutes post injecting radio-labeled composition into the duodenum of a fasted and anesthetized 230 gram rat.
Figure 3:
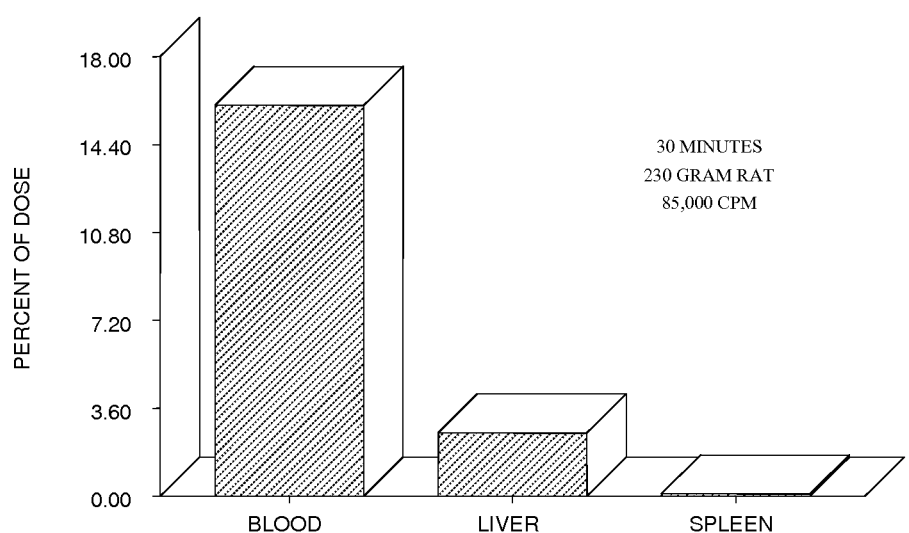
FIG. 3 is a bar graph depicting the distribution of $^{14}$C radio-labeled phospholipid amongst the blood, liver, and spleen in the rats of FIG. 2, post-sacrifice.

A 10 mg/kg body weight sample of the composition (containing 85,000 cpm of $^{14}C$ radio-label) was then injected into the duodenum of an anesthetized 230 gram fasted, but otherwise normal, rat. Blood was taken from the portal and femoral veins at 15 and 30 minutes post-dosing for counting (FIG. 2). At 30 minutes post-dosing, the rat was sacrificed and representative samples of blood, liver, and spleen were removed for analysis (FIG. 3).

Labeled constituents, as measured by $^{14}C$, were found in both portal and femoral blood of the rat. The portal blood levels of $^{14}C$ labeled constituents were higher than the femoral blood levels (FIG. 2). At 30 minutes post-dosing, approximately 15% of the constituents that were injected into the gut were found in the blood. Approximately 4% of the counts were found in the liver and about 1% were found in the spleen. Considering the relative sizes of the liver and spleen, the splenic uptake was much higher than liver uptake on a weight basis.

Experiment 2—Hepatocyte Targeting

Figure 4:
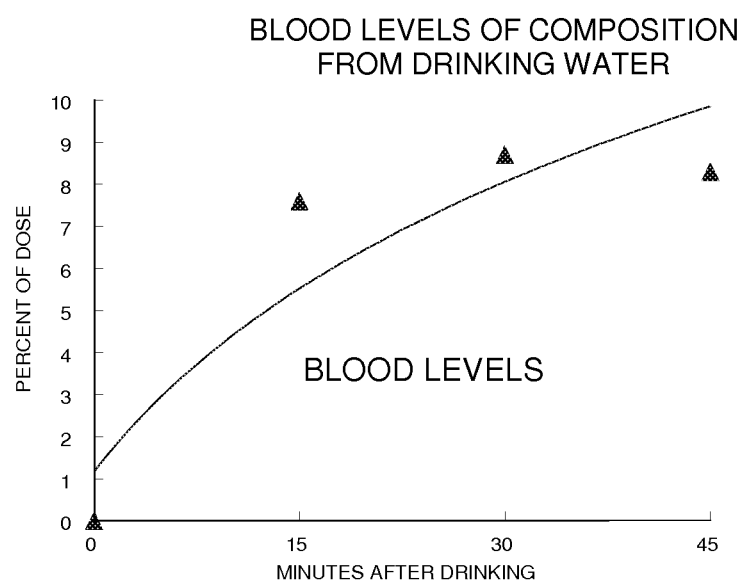
FIG. 4 is a graph depicting the absorption of radio-labeled composition from drinking water at 15, 30, and 45 minutes post-dosing.
Figure 5:
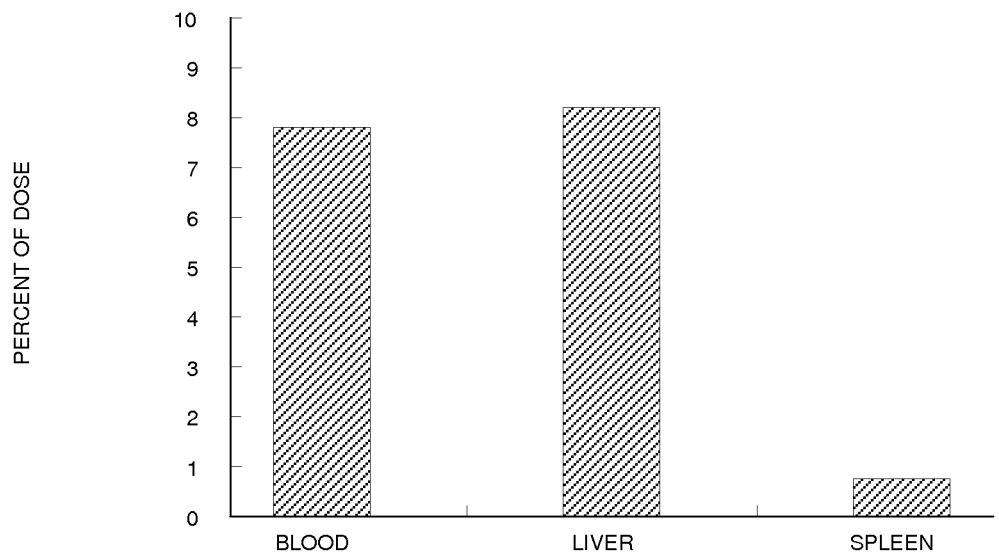
FIG. 5 is a bar graph depicting the distribution of the labeled composition amongst the blood, liver, and spleen in the rats of FIG. 4, post-sacrifice.

To demonstrate the absorption of the composition from the gut, a composition comprising insulin and constituents generated from a mixture of lipid components comprising approximately 61 mole percent 1,2 distearoyl-sn-glycero-3-phosphocholine, approximately 22 mole percent dihexadecyl phosphate, approximately 16 mole percent cholesterol, and approximately 1 mole percent poly[Cr-bis(N-2,6-diisopropylphenylcarbamoylmethyl iminodiacetic acid)] (wherein a known portion of the phospholipid component comprised $^{14}C$ labeled phospholipid) was prepared as recited in the general preparation disclosed herein. Prior to dosing, the labeled composition to rats, the rats were fasted from food for 24 hours and from water for 4 hours. The fasted rats were then permitted to drink water from a graduated water bottle containing the composition. The drinking water bottle was removed from the cage after 15 minutes, the amount of water ingested from the drinking bottle was measured, and the amount of composition ingested was calculated. The rats' blood was sampled at 15, 30, and 45 minutes and the radiolabel in each sample was counted (FIG. 4). At 45 minutes the rats were sacrificed and the livers were counted for radio-label (FIG. 5).

As is shown in FIG. 4, approximately 8% of the ingested dose was found in the rats' blood 15 minutes after the water had been removed from the cage. The quantity of constituents in the rats' blood remained constant between 15 and 45 minutes. Liver uptake was approximately 8% at 45 minutes. Splenic uptake at 45 minutes was approximately 1% of the ingested dose (FIG. 5). The total absorption was approximately 17% (including blood, liver, and spleen).

Experiment 3—Hepatocyte Targeting with a Composition in Alloxan-Streptozotocin Treated Mice Mice used in the present experiment were made diabetic by administering streptozotocin and alloxan. The diabetic animals were then divided into two groups. The control group (11 mice) was orally dosed with regular insulin. The experimental group (7 mice) was orally dosed with a composition comprising insulin and constituents generated from a mixture of lipid components comprising approximately 61 mole percent 1,2 distearoyl-sn-glycero-3-phosphocholine, approximately 22 mole percent dihexadecyl phosphate, approximately 16 mole percent cholesterol, and approximately 1 mole percent poly[Cr-bis(N-2,6-diisopropylphenylcarbamoylmethyl iminodiacetic acid)] (wherein a known portion of the phospholipid component comprised $^{14}C$ labeled phospholipid). Dosing was accomplished utilizing the water bottle dosing method described in Experiment 2.

After being made diabetic, rats in both groups were treated identically over a 7 day period and fed with plain food and plain water. Following this 7 day period, rats in the control group were treated for an additional 7 day experimental period with food and regular insulin in the available drinking water at 0.1 U/ml. Over the same 7 day experimental period, the experimental group was fed regular food with the composition of the invention available in the drinking water at 0.1 U/ml. At the end of each 7-day period, blood glucose was measured in a tail-vein sample of blood by a Beckman Blood Glucose Analyzer.

Figure 6:
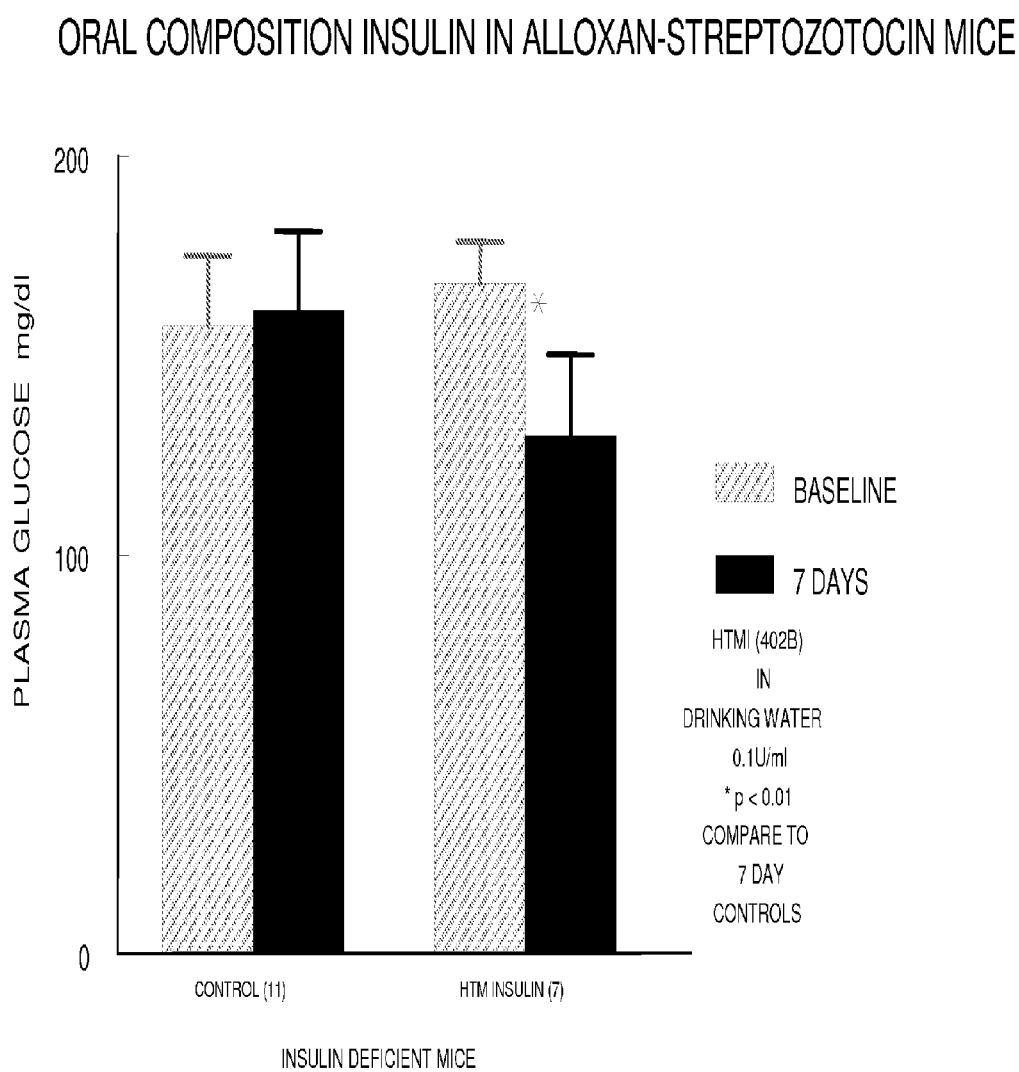
FIG. 6 is a graph depicting the efficacy of orally administered insulin in the form of a composition of the invention.

The pharmacologic efficacy of orally administered insulin in the group dosed with the above described composition is shown in FIG. 6. Mice receiving the composition had a statistically significant reduction in blood glucose on day seven ($p<0.01$) compared to mice receiving regular insulin, whose blood glucose was not altered at all.

Example 4—In Vivo Administration of Serotonin

Figure 7:
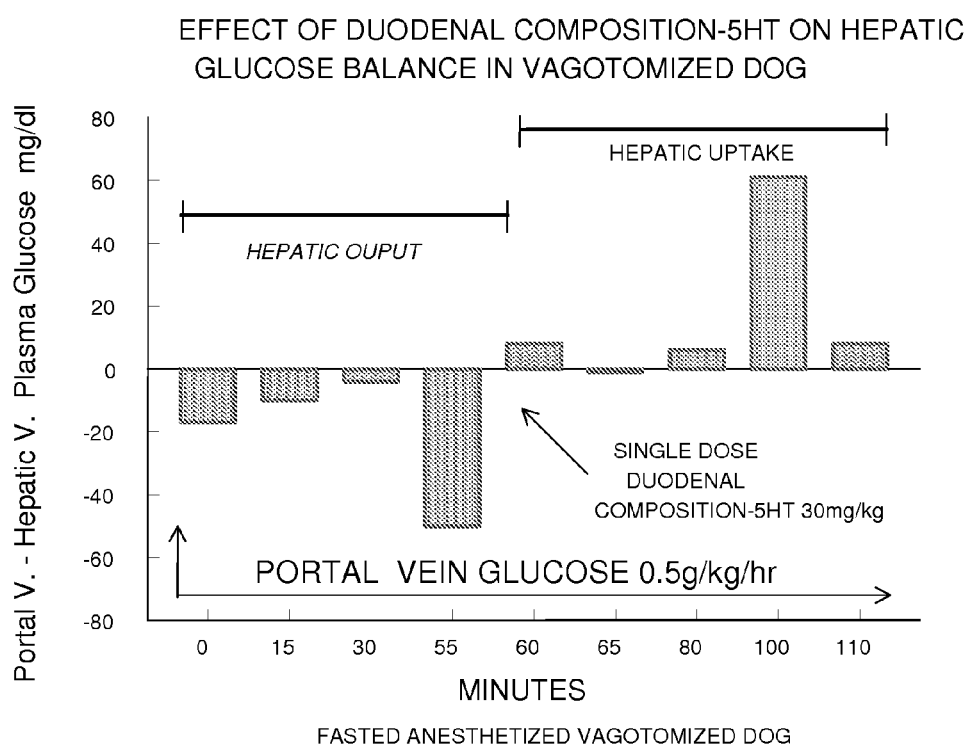
FIG. 7 is a bar graph depicting the efficacy of a composition of the invention (at low dosages), in converting a type 2 diabetic dog from hepatic glucose output to uptake during a portal glucose load.

The hepatic action of a composition comprising serotonin and constituents generated from a mixture of lipid components comprising approximately 61 mole percent 1,2 distearoyl-sn-glycero-3-phosphocholine, approximately 22 mole percent dihexadecyl phosphate, approximately 16 mole percent cholesterol, and 1 mole percent of poly[Cr-bis (N-2,6-diisopropylphenylcarbamoylmethyl iminodiacetic acid)] was demonstrated in a type 2 diabetic dog (truncal vagotomy). The dog was fasted, and then anesthetized. Blood sampling catheters were placed in the hepatic and portal veins to enable simultaneous blood sampling. Glucose was infused into the portal system at a rate of 0.5 g/kg/hour. Next, the above described composition was administered intraduodenally in a single dose of 30 µg/kg body weight. Results are depicted in FIG. 7 and demonstrate that serotonin (also referred to as 5-hydroxytryptamine or 5-HT), administered intraduodenally as a composition of the invention is effective at low doses in converting a type 2 diabetic dog from hepatic glucose output to uptake during a portal glucose load.

Example 5—In Vivo Administration of Calcitonin

Figure 8:
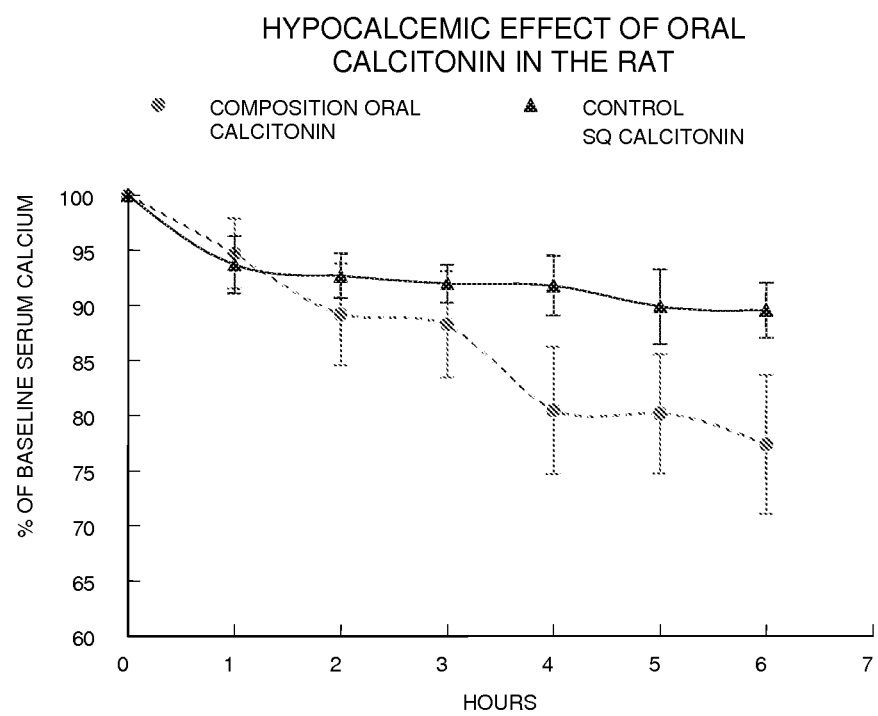
FIG. 8 is a plot of blood calcium levels after the administration of calcitonin associated with a non-targeted composition of the invention.

Normal, fasted, control rats were given a dose of salmon calcitonin via subcutaneous injection such that an initial 10% reduction in blood calcium was observed. Blood calcium levels were then measured for six hours post injection. An experimental group of rats was given the same effective dose of calcitonin by oral gavage, in the form of a composition comprising calcitonin and constituents generated from a mixture of lipid components comprising approximately 61 mole percent 1,2 disteaaroyl-sn-glycero-3-phosphocholine, approximately 22 mole percent dihexadecyl phosphate, and approximately 16 mole percent cholesterol. Blood calcium levels were followed for six hours (FIG. 8). A blood calcium reduction of up to 20% was observed in the non-control rats. This difference was statistically significant (FIG. 8).

Example 6—Clinical Trial with Targeted Insulin in Type 2 Diabetes Mellitus Subjects Capsules containing a composition of the invention were prepared. The composition comprised insulin as the therapeutic agent, gelatin, and constituents generated from a mixture of lipid components comprising approximately 61 mole percent 1,2 disteaaroyl-sn-glycero-3-phosphocholine, approximately 22 mole percent dihexadecyl phosphate, approximately 16 mole percent cholesterol, and about 1 mole percent of the sodium salt of Biotin-HDPE. Each capsule contained 2 U of insulin.

Six well characterized Type 2 diabetes patients participated in the controlled study. The patients were maintained on their customary Type 2 oral anti-diabetes therapy. Study participants were also given either placebo capsules or the above described capsules 30 minutes before a 60 gram carbohydrate meal at breakfast, lunch and dinner. Blood samples were drawn at frequent intervals over a 13 hour period and the Incremental Area Under the Curve for the blood glucose values was calculated for each subject.

Figure 10:
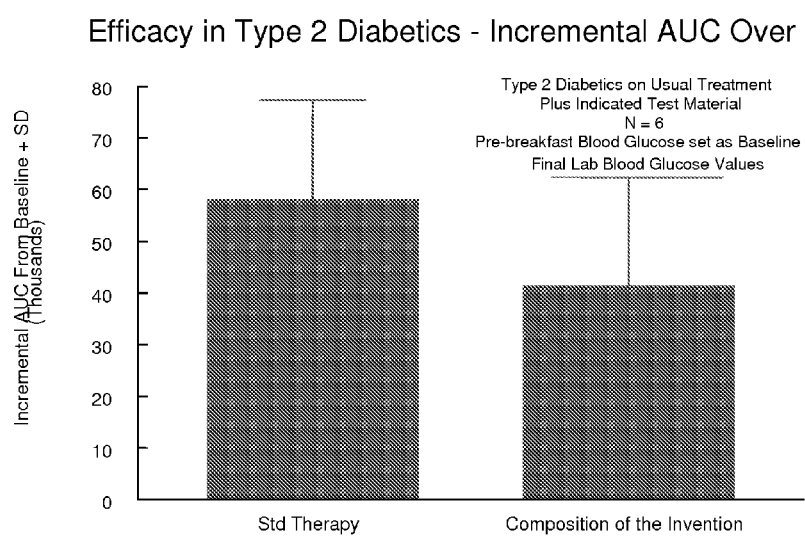
FIG. 10 is a graph of the efficacy of a composition of the invention comprising a biotin targeting agent and insulin at reducing the effects of type 2 diabetes in humans.

At 0.1 U/kg body weight/meal, the same dose that is frequently used with subcutaneous injection of insulin at a given meal, a statistically significant reduction in AUC for each of the three meals was observed. FIG. 10 depicts the results of the trial in graphical format.

Example 7—Insulin Concentration

Insulin U-500 contains 500 units of insulin/ml=0.5 units/1 µl
Add 3.36 ml of U-500 insulin to 70 ml of constituent suspension in 18 mM phosphate buffer @ pH 7.01.
(3,360 µl)*(0.5 units of insulin/µl)=1,680 units of insulin total in 73.36 ml
(1,680 units of insulin)/(73.36 ml)=22.9 units of insulin/ml—or—34.35 units of insulin/1.5 ml
Load insulin for 21 hours;
Post loading, chromatograph 1.5 ml of sample over a 1.5 cm×25 cm column with Sepharose CL-6B gel equilibrated with 18 mM phosphate buffer @ pH 7.01
0% of free insulin recovered from column; The recovery of 0% of the total loaded insulin implies that 100% of the total "loaded" insulin is associated with a constituent of the composition.
34.35 units of insulin×100%=34.35 units of insulin bound or associated with the constituents of the invention.

Figure 11:
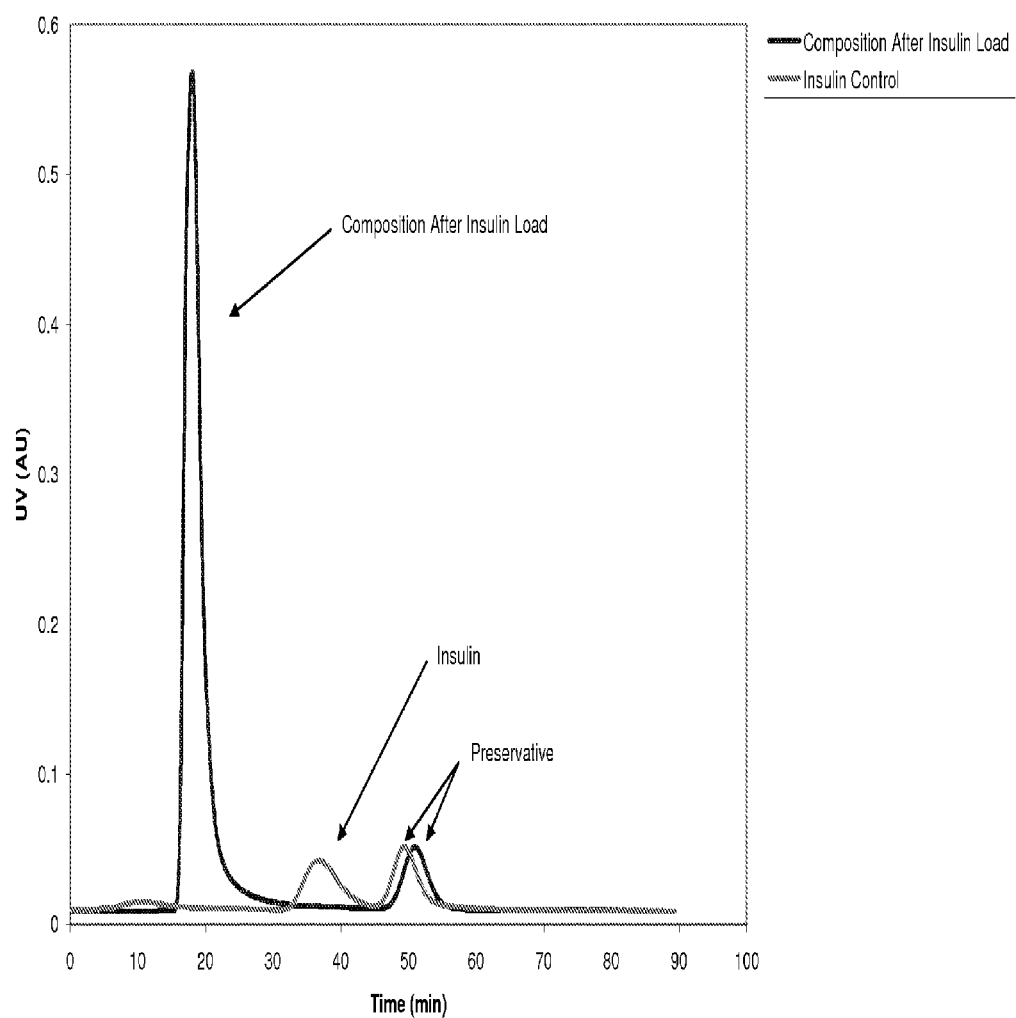
FIG. 11 is a chromatogram of a composition of the invention showing the efficacy of insulin loading.

FIG. 11 depicts the above described chromatography. A trace showing the elution time of free insulin is included for purposes of comparison. As can be seen from the chromatogram, insulin is associated with the constituents of the invention and no free insulin is in solution. A preservative included with insulin does not associate with the constituents of the composition of the invention and is visible in the chromatogram.

Example 8—Oral Delivery of GLP-1

Rats were fasted overnight. Subsequently, 800 mg each of alloxan and streptozotocin were dissolved in 40 mL of PBS (pH 7, 0.01 M). The fasted rats were then treated immediately with a 0.5 mL IP dose to induce insulin deficiency. The animals were then stabilized overnight with water and food. Following stabilization, the rats were fasted overnight to deplete liver glycogen.

Subsequently, 1.5 g glucose/kg body weight and GLP-1 in the form of a GLP-1/constituent construct were simultaneously administered via oral gavage. The constituents were prepared from a mixture of lipid components comprising approximately 61 mole percent 1,2 disteaaroyl-sn-glycero-3-phosphocholine, approximately 22 mole percent dihexadecyl phosphate, and approximately 16 mole percent cholesterol ("associated GLP-1"). In separate experiments, the amount of associated GLP-1 was varied. Liver glycogen was measured chemically at 2 hours post dosing.

As a control, unassociated GLP-1 was gavaged in place of associated GLP-1. In a separate control, GLP-1, in a dose similar to that orally gavaged, was injected intraperitoneally.

As is shown in Table 3, below, substantially enhanced oral efficacy was observed for the associated GLP-1 versus non-associated GLP-1.

TABLE 3

| Treatment | Dose GLP-1 mg/rat | Liver Glycogen mg/g liver |
|---|---|---|
| Control Oral GLP-1 | 0.01 | 40 ± 22 |
| Intraperitoneal GLP-1 | 0.01 | 59 ± 44 |
| Oral Associated GLP-1 | 0.005 | 73 ± 56* |
| Oral Associated GLP-1 | 0.01 | 90 ± 75* |

*p = 0.05 compared to Control Oral GLP-1

Example 9—Oral IgG

Human IgG antibodies were covalently attached to a constituent of the invention, as described previously herein ("covalent IgG"). Subsequently, eight 250 gram laboratory rats were prepared with intra-duodenal catheters for the administration of covalent IgG. After an overnight fast, 5 ug of covalent IgG was infused into the duodenal catheter. The catheter was subsequently washed with 0.5 ml buffer. Blood samples were taken at 15, 30, 60 and 120 minutes to assay the plasma concentration of human IgG antibodies by ELISA reaction.

In a control experiment, 5 ug of free IgG was infused into the duodenal catheter. The catheter was subsequently washed with 0.5 ml buffer. Blood samples were taken at 15, 30, 60 and 120 minutes to assay the plasma concentration of human IgG antibodies by ELISA reaction. The results of both studies are shown in FIG. 12.

Figure 12:
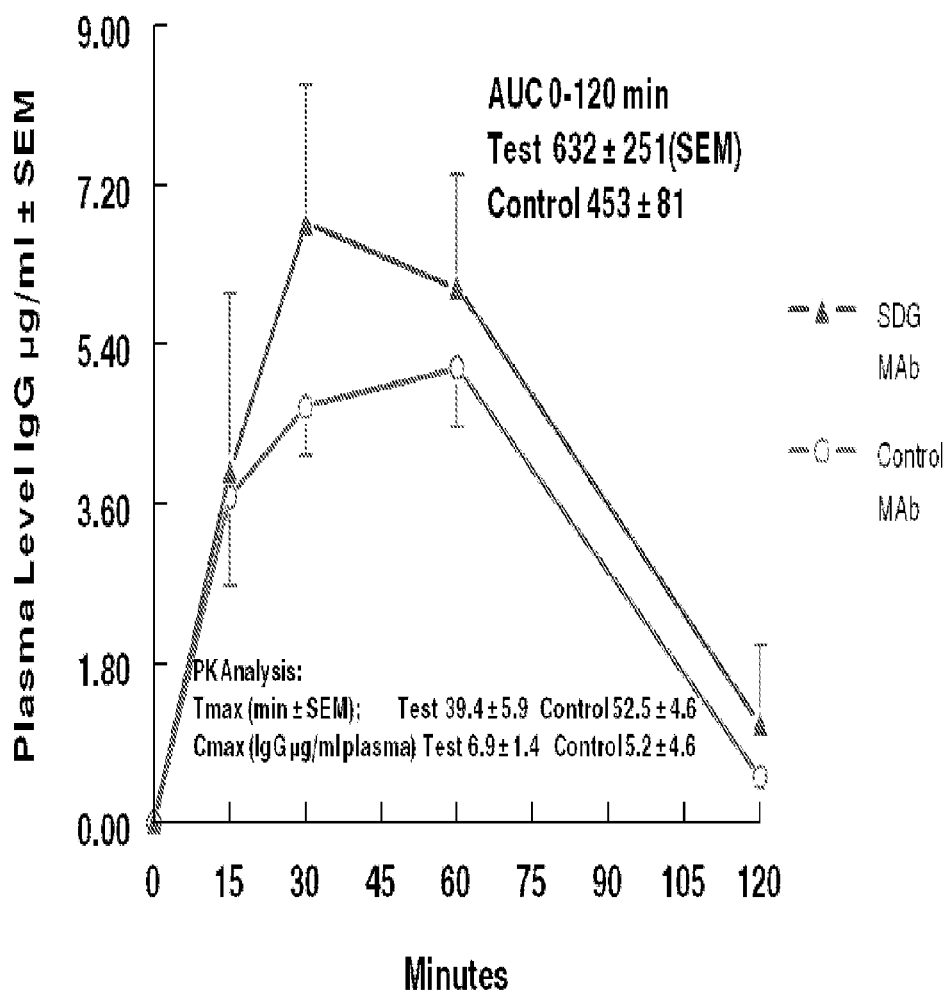
FIG. 12 is a graph depicting the efficacy of oral delivery of IgG antibodies covalently linked to a composition of the invention versus oral absorption of non-associated (free) IgG antibodies.

As can be seen in FIG. 12, covalent IgG provided enhanced plasma concentration of human IgG (AUC) as compared to free IgG. Likewise, covalent IgG enhanced Tmax—the time to maximum concentration, and Cmax—the maximum plasma concentration observed upon dosing. The enhanced efficacy of covalent IgG, as compared to free IgG, thus demonstrates the ability of a compound of the invention to enhance oral absorption of very large proteins into the systemic circulation.

Example 10—Oral Thyroxine

Thyroxine is known to lower blood cholesterol and triglyceride levels. However, at the doses required to treat high cholesterol and triglyceride, thyroxine causes hyperthyroidism as an unwanted side effect. The goal of this study was to demonstrate that orally administered targeted thyroxine associated with a compound of the invention would act at the liver with the result of lowering blood lipids without inducing the unwanted hyperthyroidism.

Normal laboratory mice, on high caloric diets, were administered low oral doses (0.2 to 1.0 µg) thyroxine in the form of a composition comprising thyroxine and constituents generated from a mixture of lipid components comprising approximately 61 mole percent 1,2 distearoyl-sn-glycero-3-phosphocholine, approximately 22 mole percent dihexadecyl phosphate, approximately 16 mole percent cholesterol, and approximately 1 mole percent of the sodium salt of Biotin-HDPE, a liver-targeting agent.

Figure 13:
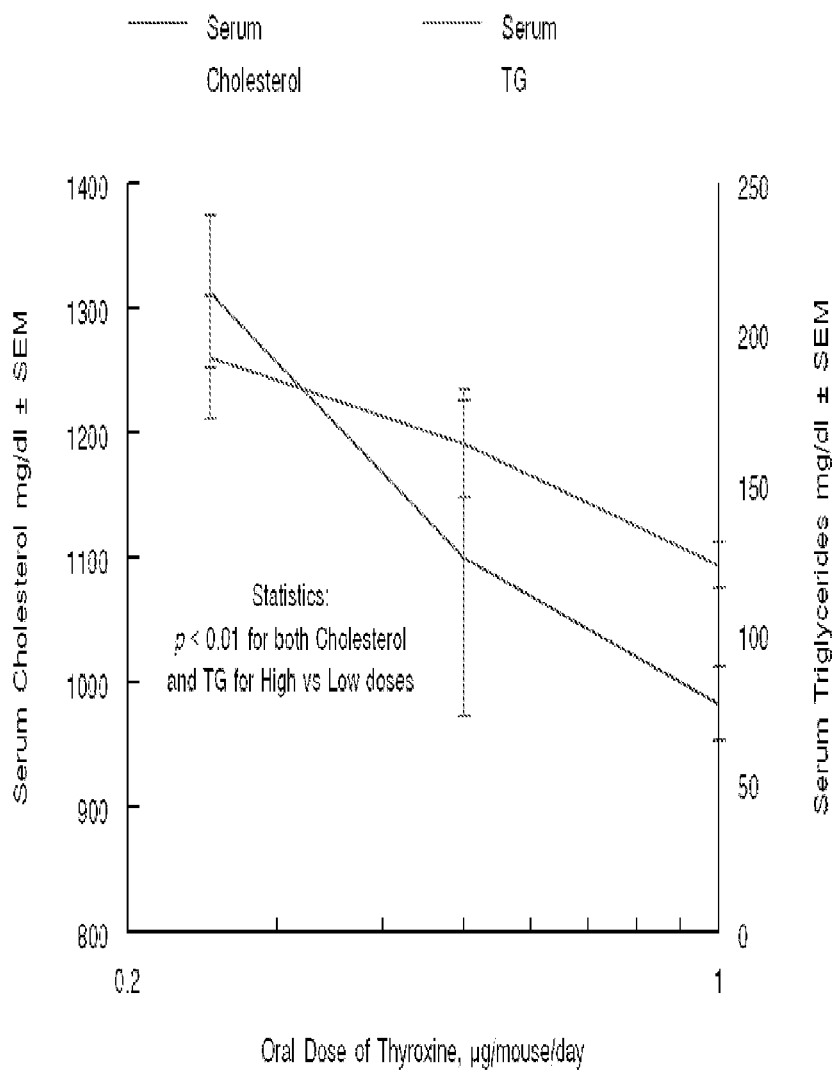
FIG. 13 is a graph depicting the effect of oral administration of thyroxine associated with a composition of the invention on serum cholesterol and triglycerides ("TG") in mice.

The mice, in groups of 4, were dosed daily by oral gavage for one week in a dose response study. Blood cholesterol and triglycerides were measured after one week treatment. Baseline values for cholesterol and triglycerides for all the groups were similar. The dose responses, shown in FIG. 13, demonstrates the efficacy of orally administered, hepatic targeted thyroxine associated with a composition of the invention. Blood levels of thyroid hormone did not increase with the dosing of hepatic targeted oral thyroxine, demonstrating the safety of the product.

Other published studies (Erion, M., et al., PNAS Sep. 25, 2007 vol 104, #39, pp 15490-15495) with hepatic targeted thyroxine analogs required doses at least 10 fold higher than those described herein to elicit similar reductions in blood cholesterol and triglycerides.

Example 11—Oral Interferon

A composition was prepared comprising interferon-α as the therapeutic agent and constituents generated from a mixture of lipid components comprising approximately 61 mole percent 1,2 distearoyl-sn-glycero-3-phosphocholine, approximately 22 mole percent dihexadecyl phosphate, approximately 16 mole percent cholesterol, and about 1 mole percent of the sodium salt of Biotin-HDPE.

Six patients with Hepatitis C, genotype 3, were treated with an aqueous suspension of the above described composition and Ribivirin daily for 8 weeks. The interferon-α dose in the aqueous suspension of the composition was 60,000 Units/day.

Figure 14:
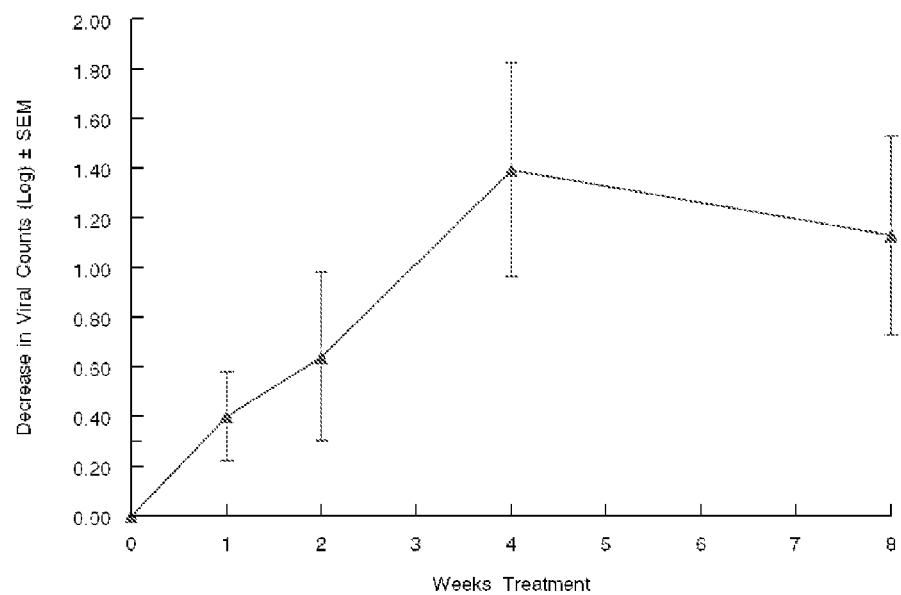
FIG. 14 is a graph depicting the effect of oral administration of interferon associated with a composition of the invention on reducing viral load in humans suffering from hepatitis-C.

Hepatitis C viral loads were measured at the beginning of the study, then at weeks 1, 2, 4, and 8. See FIG. 14. The data demonstrates the ability of the aqueous suspension of a composition of the invention to lower viral load with a minimal dose of interferon. Side effects were likewise minimized.

Example 12—Clinical Trial in Type 2 Diabetes Mellitus Subjects

An 18 week study was designed to review the efficacy of a compound of the invention for controlling blood glucose levels in Type 2 diabetics. Data for patients administered a composition comprising insulin, i.e. the non-control group is not reported herein. Data for the control group, i.e. patients administered a composition of the invention without insulin, is presented below.

Capsules containing a composition of the invention were prepared for the control group. The composition provided to the control group comprised gelatin (230 mg), approximately 61 mole percent 1,2 distearoyl-sn-glycero-3-phosphocholine (3.36 mg), approximately 22 mole percent dihexadecyl phosphate (0.86 mg), approximately 16 mole percent cholesterol (0.44 mg), and about 1 mole percent of the sodium salt of Biotin DHPE (0.075 mg).

A variable Baseline Stabilization Phase of up to 12 weeks was deployed to stabilize patients on background metformin therapy. All patients previously treated with metformin therapy for a minimum of 12 weeks directly entered into the study at the end of Baseline Stabilization Period 7-point glucose testing described below. Naïve treatment diabetic patients or patients on metformin in combination with other OADs were placed on metformin alone and stabilized on the mono-therapy for 12 weeks. At the end of the Baseline Stabilization Period, the patient underwent two consecutive days of 7-point blood glucose tests (Days −1 and 0). The 7-point glucose tests results were recorded on Patient Diaries.

Patients entered the "Treatment Phase" of the study once they optimized their metformin dosing regimen. This was Day 1 of the Treatment Phase. At the Day 1 Visit, Baseline HbA1c levels were obtained. Following the Baseline Stabilization Phase, patients were administered the above described capsules. Patients on the "low dose" (78 µg biotin daily) were given one capsule per dose, with four doses daily (10-30 minutes before breakfast, 10-30 minutes before lunch, 10-30 minutes before dinner, and 10-30 minutes before bed time). Patients on the "high dose" (234 µg biotin daily) were given three capsules per dose, with the same dosing schedule as the low dose patients. During the Treatment Phase, patients were instructed to follow the ADA "weight maintenance diet".

Figure 15:
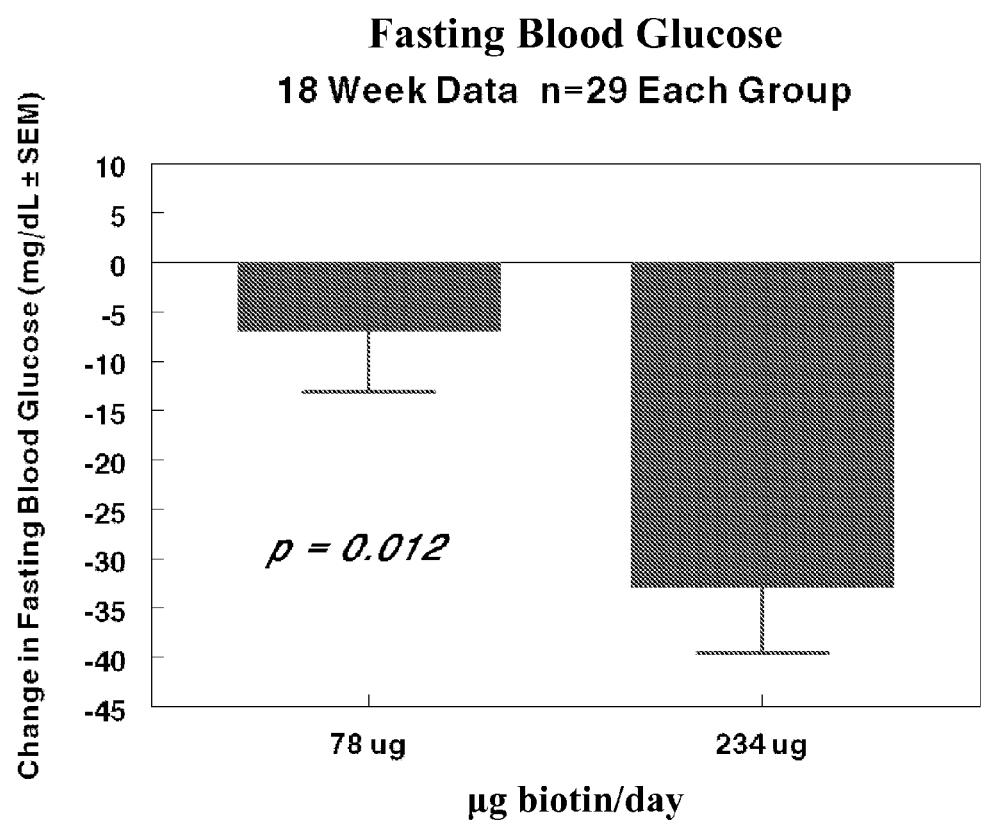
FIG. 15 is a bar graph depicting the effect of various amounts of a composition of the invention on fasting blood glucose after an 18 week dosing regimen.
Figure 16:
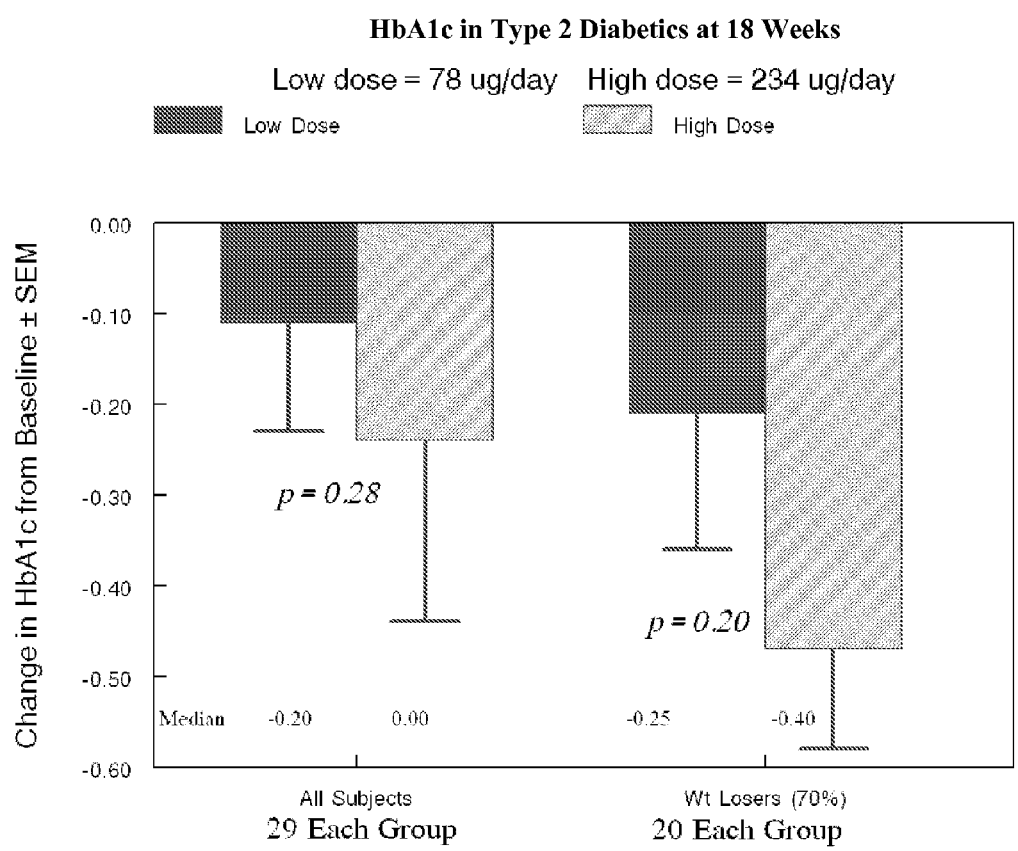
FIG. 16 is a bar graph depicting the effect of various amounts of a composition of the invention on HbA1c in Type 2 diabetics after an 18 week dosing regimen.

At the end of Week 2 (Day 14), patients performed a 7-point glucose test. At the end of Week 4 (Days 27 and 28), patients performed 7-point glucose tests and returned to the clinic for the Week 4 visit (Day 29). At this visit, an HbA1c level was obtained. Patients continued in the study with site visits at Week 8 (Day 57), with 7-point glucose test performed on Days 55 and 56 and Week 12 (Day 85), with 7-point glucose tests on Days 83 and 84. On Days 57 and 85, an HbA1c level was obtained. The Week 18 Visit was conducted on Day 127 with the 7-point glucose test performed on Days 125 and 126. An HbA1c level was also obtained at this visit. After 18 weeks, patients dosed with a therapeutic agent free composition of the invention experienced a reduction in fasting blood glucose of about 7 mg/dl (low dose) and about 35 mg/dl (high dose). See, for example, FIG. 15. All patients in the study, at both the high and low dose, showed reduced HbA1c concentrations at 18 weeks, as shown in FIG. 16.

Figure 19:
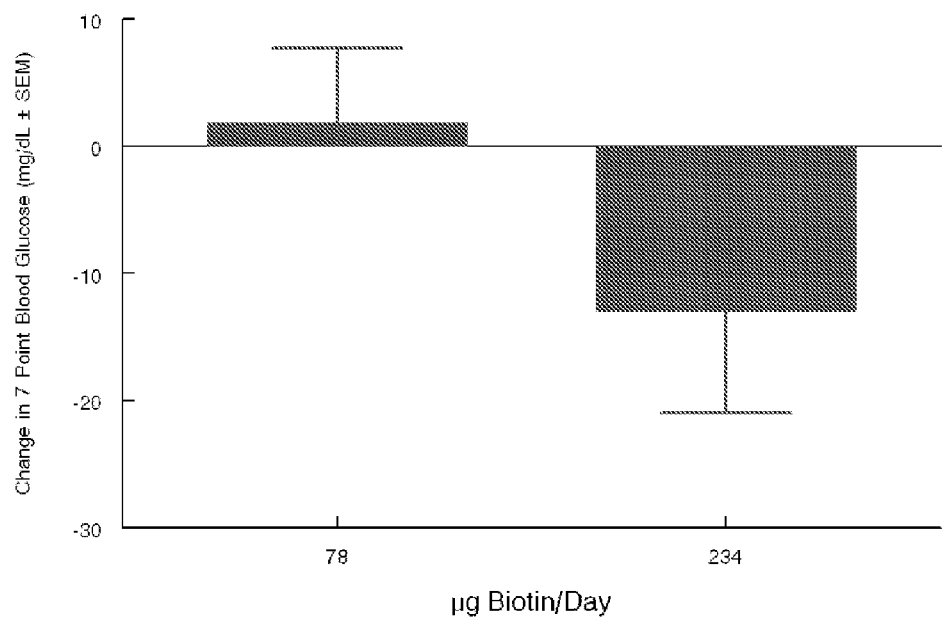
FIG. 19 is a graph of the 7 point blood glucose index of the "Intent To Treat" population as of the last observation carried forward ("LOCF") with a composition of the invention.

Data obtained at the 18 week time point (intent to treat population) for the 7-point glucose test showed a slight increase for the low dose population, but a statistically significant reduction of about 10 mg/dl in the high dose population. The data is represented graphically in FIG. 19.

Figure 17:
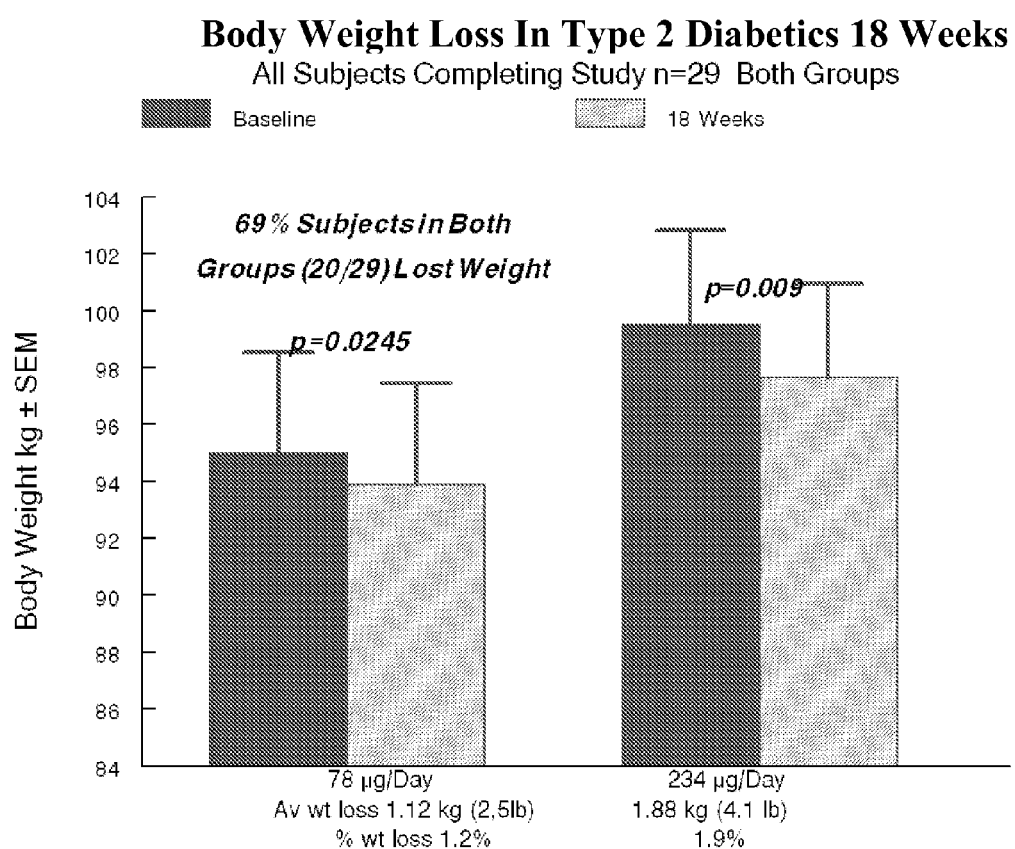
FIG. 17 is a bar graph depicting weight loss in a total population of patients dosed with various amounts of a composition of the invention after an 18 week dosing regimen.

In addition to the above, after 18 weeks, patients on the low dose, on average, lost about 1.2% of their total body mass, while patients on the high dose lost approximately 1.9% of their total body mass. About 69% of subjects in the study observed some weight loss. These data are shown graphically in FIG. 17.

Figure 18:
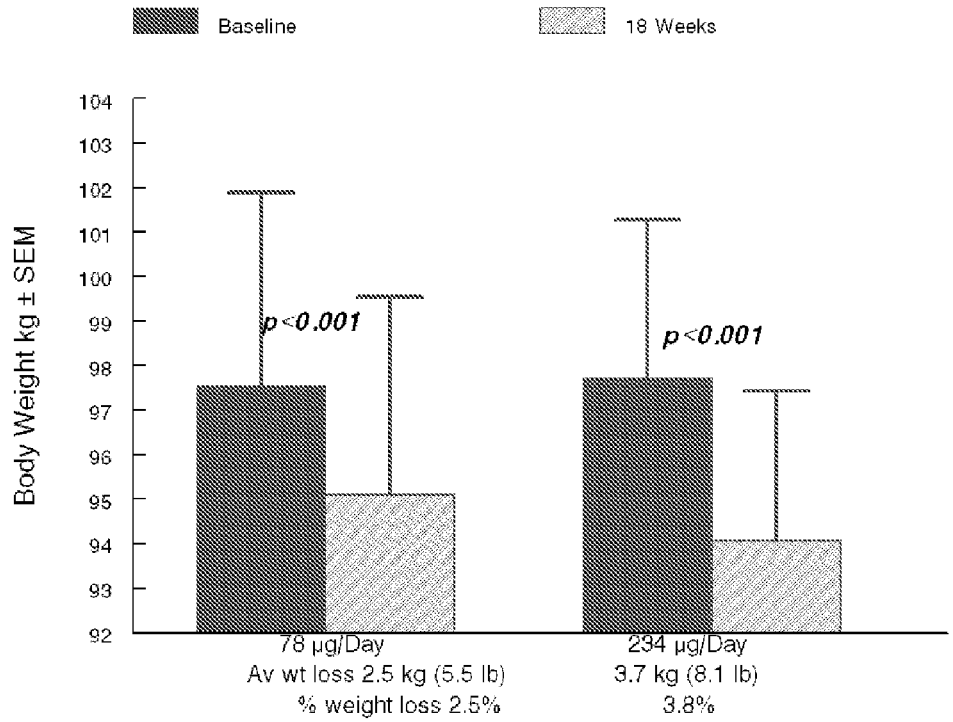
FIG. 18 is a bar graph depicting weight loss in a subpopulation of patients dosed with various amounts of a composition of the invention after an 18 week dosing regimen.

When the 18 week weight loss data was analyzed to exclude those patients who lost no weight, the average weight loss for low dose patients was approximately 2.5% of total body mass, while high dose patients lost, on average, about 3.8% of their total body mass. These data are represented graphically in FIG. 18.

Figure 20:
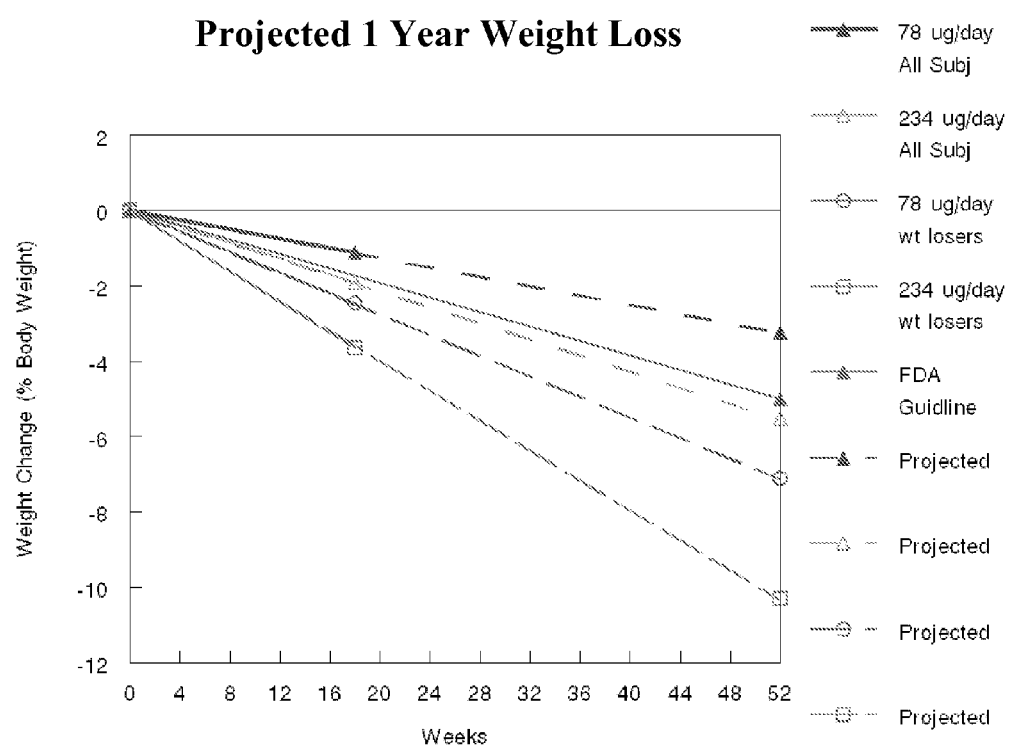
FIG. 20 is a line graph showing the expected weight loss over a 1 year period in a population of patients dosed with various amounts of a composition of the invention.

Various curves extrapolating total weight loss over 1 year were created based on the 18 week weight loss data. See FIG. 20. It is evident, based on the extrapolated data, that high dose patients who respond to the composition of the invention, could lose up to about 10% of their total body weight in one year. Low dose patients could similarly lose about 6 to about 7% of their total body weight.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An orally bioavailable composition for inducing weight loss, the composition comprising gelatin and additional constituents, wherein the additional constituents consist consists of about 56 mole percent 1,2-distearoyl-sn-glycero-3-phosphocholine, about 21 mole percent dihexadecyl phosphate, about 15 mole percent cholesterol, and about 8 mole percent of a biotin-derived targeting agent, wherein the additional constituents are the only weight loss-inducing ingredients in the composition.

2. The composition of claim 1, wherein said biotin-derived targeting agent is selected from the group consisting of N-hydroxysuccinimide (NHS) biotin; sulfo-NHS-biotin; N-hydroxysuccinimide long chain biotin; sulfo-N-hydroxysuccinimide long chain biotin; D-biotin; biocytin; sulfo-N-hydroxysuccinimide-S—S-biotin; biotin-BMCC; biotin-HPDP; iodoacetyl-LC-biotin; biotin-hydrazide; biotin-LC-hydrazide; biocytin hydrazide; biotin cadaverine; carboxybiotin; photobiotin; p-aminobenzoyl biocytin trifluoroacetate; p-diazobenzoyl biocytin; biotin DHPE; biotin-X-DHPE; 12-((biotinyl)amino)dodecanoic acid; 12-((biotinyl)amino)dodecanoic acid succinimidyl ester; S-biotinyl homocysteine; biocytin-X; biocytin x-hydrazide; biotinethylenediamine; biotin-XL; biotin-X-ethylenediamine; biotin-XX hydrazide; biotin-XX-SE; biotin-XX, SSE; biotin-X-cadaverine; α-(t-BOC)biocytin; N-(biotinyl)-N'-(iodoacetyl) ethylenediamine; DNP-X-biocytin-X-SE; biotin-X-hydrazide; norbiotinamine hydrochloride; 3-(N-maleimidylpropionyl)biocytin; ARP; biotin-1-sulfoxide; biotin methyl ester; biotin-maleimide; biotin-poly(ethyleneglycol)amine; (+) biotin 4-amidobenzoic acid sodium salt; Biotin 2-N-acetylamino-2-deoxy-β-D-glucopyranoside; Biotin-α-D-N-acetylneuraminide; Biotin-α-L-fucoside; Biotin lacto-N-bioside; Biotin-Lewis-A trisaccharide; Biotin-Lewis-Y tetrasaccharide; Biotin-α-D-mannopyranoside; biotin 6-O-phospho-α-D-mannopyranoside; and 1,2-dipalmitoyl-sn-glycero-3-phosphoethanolamine-N-(biotinyl), iminobiotin derivatives of the aforementioned compounds, and any mixtures thereof.

3. The composition of claim 2, wherein said biotin-derived targeting agent is D-biotin, biotin DHPE, or biotin-X-DHPE.

4. The composition of claim 1, said composition further comprising D-biotin.

5. A food additive, dietary supplement, or beverage additive for inducing weight loss, wherein the food additive, dietary supplement, or beverage additive comprises comprising gelatin and additional constituents, wherein the additional constituents consist of about 56 mole percent 1,2-distearoyl-sn-glycero-3-phosphocholine, about 21 mole percent dihexadecyl phosphate, about 15 mole percent cholesterol, and about 8 mole percent of a targeting agent, wherein the additional constituents are the only weight loss-inducing ingredients in the food additive, dietary supplement, or beverage additive.

6. The food additive, dietary supplement, or beverage additive of claim 5, wherein said biotin-derived targeting agent is selected from the group consisting of N-hydroxysuccinimide (NHS) biotin; sulfo-NHS-biotin; N-hydroxysuccinimide long chain biotin; sulfo-N-hydroxysuccinimide long chain biotin; D-biotin; biocytin; sulfo-N-hydroxysuccinimide-S—S-biotin; biotin-BMCC; biotin-HPDP; iodoacetyl-LC-biotin; biotin-hydrazide; biotin-LC-hydrazide; biocytin hydrazide; biotin cadaverine; carboxybiotin; photobiotin; p-aminobenzoyl biocytin trifluoroacetate; p-diazobenzoyl biocytin; biotin DHPE; biotin-X-DHPE; 12-((biotinyl)amino)dodecanoic acid; 12-((biotinyl)amino)dodecanoic acid succinimidyl ester; S-biotinyl homocysteine; biocytin-X; biocytin x-hydrazide; biotinethylenediamine; biotin-XL; biotin-X-ethylenediamine; biotin-XX hydrazide; biotin-XX-SE; biotin-XX, SSE; biotin-X-cadaverine; α-(t-BOC)biocytin; N-(biotinyl)-N'-

(iodoacetyl) ethylenediamine; DNP-X-biocytin-X-SE; biotin-X-hydrazide; norbiotinamine hydrochloride; 3-(N-maleimidylpropionyl)biocytin; ARP; biotin-1-sulfoxide; biotin methyl ester; biotin-maleimide; biotin-poly(ethyleneglycol)amine; (+) biotin 4-amidobenzoic acid sodium salt; Biotin 2-N-acetylamino-2-deoxy-β-D-glucopyranoside; Biotin-α-D-N-acetylneuraminide; Biotin-α-L-fucoside; Biotin lacto-N-bioside; Biotin-Lewis-A trisaccharide; Biotin-Lewis-Y tetrasaccharide; Biotin-α-D-mannopyranoside; biotin 6-O-phospho-α-D-mannopyranoside; and 1,2-dipalmitoyl-sn-glycero-3-phosphoethanolamine-N-(biotinyl), iminobiotin derivatives of the aforementioned compounds, and any mixtures thereof.

7. The food additive, dietary supplement, or beverage additive of claim 6, wherein said biotin-derived targeting agent is D-biotin, biotin DHPE, or biotin-X-DHPE.

8. A method of making an orally bioavailable composition for inducing weight loss, the composition comprising gelatin and additional constituents, wherein the additional constituents consist of about 56 mole percent 1,2 distearoyl-sn-glycero-3-phosphocholine, about 21 mole percent dihexadecyl phosphate, about 15 mole percent cholesterol, and about 8 mole percent of a biotin-derived targeting agent, wherein the additional constituents are the only weight loss-inducing ingredients in the composition, said method comprising:

mixing said 1,2 distearoyl-sn-glycero-3-phosphocholine, di hexadecyl phosphate, cholesterol and said at least one biotin-derived targeting agent in aqueous media to form a mixture;

adding said mixture to gelatin to form a gelatin-associated mixture; and drying said gelatin-associated mixture.

9. The method of claim 8, wherein said biotin-derived targeting agent is selected from the group consisting of D-biotin, biotin DHPE, and biotin-X-DHPE.

\* \* \* \* \*